(12) United States Patent
Prystupa et al.

(10) Patent No.: US 11,871,698 B2
(45) Date of Patent: Jan. 16, 2024

(54) CROP GROWTH SYSTEM INCLUDING A SEEDER AND ASSOCIATED HARVESTER

(71) Applicant: 10691976 Canada Ltd., Winnipeg (CA)

(72) Inventors: David Prystupa, Pinawa (CA); John Pacak, Winnipeg (CA)

(73) Assignee: 10691976 Canada Ltd., Winnipeg (CA)

( * ) Notice: Subject to any disclaimer, the term of this patent is extended or adjusted under 35 U.S.C. 154(b) by 1216 days.

(21) Appl. No.: 16/360,743

(22) Filed: Mar. 21, 2019

(65) Prior Publication Data

US 2019/0289774 A1 Sep. 26, 2019

Related U.S. Application Data

(60) Provisional application No. 62/646,211, filed on Mar. 21, 2018, provisional application No. 62/646,202, filed on Mar. 21, 2018.

(51) Int. Cl.
*A01D 43/14* (2006.01)
*A01D 41/127* (2006.01)
(Continued)

(52) U.S. Cl.
CPC ........ *A01D 41/1277* (2013.01); *A01B 79/005* (2013.01); *A01C 7/04* (2013.01); *A01C 7/124* (2013.01); *A01C 7/128* (2013.01); *A01C 7/18* (2013.01); *A01C 7/20* (2013.01); *A01C 21/007* (2013.01); *A01D 43/14* (2013.01); *A01F 12/18* (2013.01); *A01F 12/44* (2013.01); *A01F 12/60* (2013.01); *G01N 33/025* (2013.01);
(Continued)

(58) Field of Classification Search
CPC ....... A01D 41/1277; A01D 43/14; A01C 7/20
See application file for complete search history.

(56) References Cited

U.S. PATENT DOCUMENTS 4,943,260 A * 7/1990 Fossum .................. A01F 12/00
209/241
5,173,079 A * 12/1992 Gerrish .............. A01D 41/1272
56/DIG. 15
(Continued)

FOREIGN PATENT DOCUMENTS

| CA | 2474390 | | 5/2005 | | |
|---|---|---|---|---|---|
| CA | 2856418 | A1 * | 5/2013 | ........... | A01B 79/005 |

(Continued)

*Primary Examiner* — Alicia Torres
(74) *Attorney, Agent, or Firm* — Adrian D. Battison; Ryan W. Dupuis; Ade & Company Inc.

(57) ABSTRACT

A method for growing plants includes both a seeder and a harvester both of which include arrangements for singulating the seeds and for measuring parameters of the seeds while singulated. This can be used for seeding selected seeds and for harvesting particular plants. The system operates by correlating information from the individual seeded seeds and from the harvested seeds in respect of a particular location on the growth medium and may include information relating the growth medium at the location. The location can be determined by seeding the plants in patterns which can be detected by a reader on the harvester. The system can be used to control selection of seeds to take into account soil conditions at the plant.

19 Claims, 16 Drawing Sheets

(51) Int. Cl.
  *A01F 12/44* (2006.01)
  *A01F 12/60* (2006.01)
  *A01C 7/04* (2006.01)
  *A01C 7/12* (2006.01)
  *A01C 7/18* (2006.01)
  *A01C 7/20* (2006.01)
  *A01B 79/00* (2006.01)
  *A01C 21/00* (2006.01)
  *A01F 12/18* (2006.01)
  *G01N 33/02* (2006.01)
  *A01C 7/06* (2006.01)
  *A01B 49/00* (2006.01)
  *A01C 7/08* (2006.01)
  *A01C 7/00* (2006.01)
  *A01C 5/06* (2006.01)

(52) U.S. Cl.
  CPC .............. *A01B 49/00* (2013.01); *A01C 5/064* (2013.01); *A01C 7/002* (2013.01); *A01C 7/06* (2013.01); *A01C 7/08* (2013.01)

(56) References Cited

U.S. PATENT DOCUMENTS

| | | | |
|---|---|---|---|
| 5,176,573 A * | 1/1993 | Dow | A01D 45/02 460/48 |
| 5,787,825 A | 8/1998 | Yaji | |
| 5,987,384 A | 11/1999 | Matson | |
| 5,991,025 A | 11/1999 | Wright et al. | |
| 6,070,539 A | 6/2000 | Flamme | |
| 6,681,706 B2 | 1/2004 | Sauder | |
| 7,185,596 B2 | 3/2007 | Thiemke | |
| 7,765,780 B2 | 8/2010 | Koselka | |
| 7,882,686 B2 | 2/2011 | Bryan, Jr. | |
| 8,393,137 B1 * | 3/2013 | Crosby | A01F 15/0825 701/50 |
| 9,603,299 B2 | 3/2017 | Wendte | |
| 10,701,856 B2 | 7/2020 | Koch et al. | |
| 2011/0047042 A1 | 2/2011 | Blickhan et al. | |
| 2013/0124239 A1 | 5/2013 | Rosa et al. | |
| 2015/0216110 A1 | 8/2015 | Harmelink et al. | |
| 2016/0071410 A1 | 3/2016 | Rupp | |
| 2016/0212931 A1 | 7/2016 | Henry | |
| 2016/0302353 A1 | 10/2016 | Wendte | |
| 2017/0049044 A1 | 2/2017 | Stoller et al. | |
| 2017/0089742 A1 | 3/2017 | Bruns | |
| 2017/0188512 A1 | 7/2017 | Fromm | |
| 2017/0196171 A1 | 7/2017 | Xu et al. | |
| 2018/0035622 A1 | 2/2018 | Gresch et al. | |
| 2019/0183066 A1 | 6/2019 | Conrad | |

FOREIGN PATENT DOCUMENTS

| | | | |
|---|---|---|---|
| CA | 2880570 | 2/2014 | |
| CA | 2924862 | 12/2016 | |
| CA | 3029134 | 6/2017 | |
| CA | 2966695 | 12/2017 | |
| CN | 109328652 | 2/2019 | |
| DE | 19845860 | 4/2000 | |
| EP | 1346622 A1 * | 9/2003 | ........... A01B 79/005 |
| EP | 2143316 A1 * | 1/2010 | ........... A01D 41/127 |
| EP | 2902957 | 8/2015 | |
| FR | 2580895 | 10/1986 | |
| JP | 3073911 | 12/2000 | |
| KR | 200363777 | 10/2004 | |
| KR | 20150124154 | 11/2015 | |
| KR | 20150052433 A * | 12/2015 | |
| WO | WO2014130523 | 8/2014 | |
| WO | WO2018018155 | 2/2018 | |

* cited by examiner

→ AAAAABBAABAA

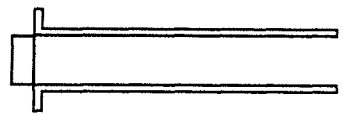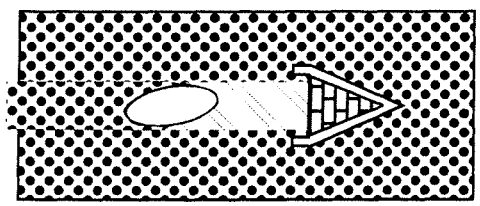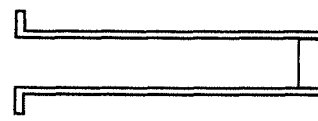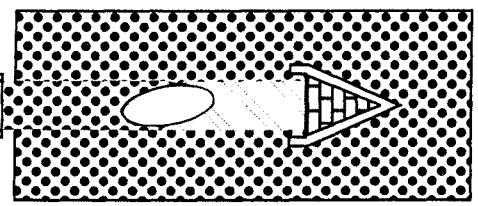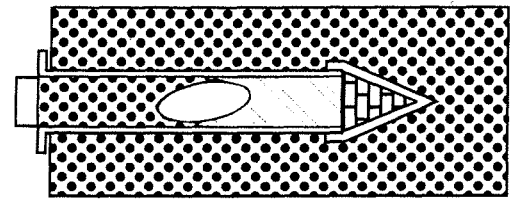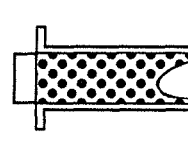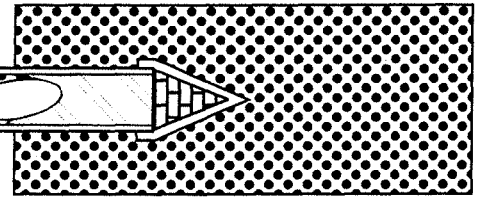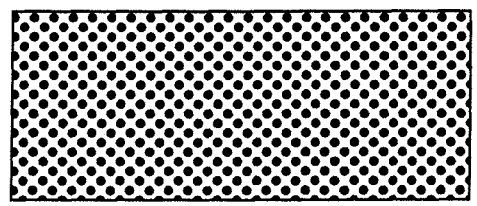

CROP GROWTH SYSTEM INCLUDING A SEEDER AND ASSOCIATED HARVESTER

This application claims the benefit under 35 USC 119 (e) from Provisional applications 62/646,202 and 62/646,211 both filed Mar. 21, 2018, the disclosures of which are incorporated herein by reference.

This invention relates to a crop growing system which includes a seeding system and a harvesting system which can be operated separately or may form parts of a common system which cooperate together to provide control of seeding and harvesting of a crop which is not currently possible.

The system provides a method and device for placing particles on a substrate primarily in a seeding action. The substrate may be the ground or other growth medium. The seeding apparatus moves over the ground or growth medium or vice versa where the growth medium is moved past a stationary seeding system for example in indoor agriculture. The system provides a method and device for harvesting particles from the growth substrate or ground and and sorting the particles based on one or more measured properties. The invention is primarily directed toward placing seed and fertilizer particles in an agricultural field and subsequently harvesting, but the invention is not limited to seeds and fertilizer on a field, other types of particles and substrates may be used.

BACKGROUND OF THE INVENTION

Agricultural machines are widely used to plant seeds in a field. It is important to select seed that is of the right type, has a high probability of germinating and producing a viable plant, and to place each seed in a location that maximizes yield potential. Furthermore, the planting operation may include placing other materials such as fertilizer, herbicide, pesticide, biological control agents or spatial markers spatially proximate to seed locations.

The prior art has gone only part way in realizing these objectives. Planters are typically used to place relatively large seeds such as corn at pre-determined intervals in a row one seed at a time with typical density in the range of 3 to 7 seeds per meter. There has been a push by major manufactures to increase the planter speed without loss of seed placement precision. At the time of writing (2018), all major brands have a top speed of about 10 mph (15 kph) and place about 14 seeds per second. Recent planters typically contain a singulator disk with a series of holes at regular intervals along the periphery that attract seeds from a reservoir by vacuum. This approach has several drawbacks. The speed of the planter is limited by the speed of the singulator. The vacuum required by the singulator is costly in both equipment and power to run the equipment. Finally, the singulator is prone to failure by three modes. First, a singulator hole may fail to attract a seed resulting in a lower density of plants and a lower yield. The probability of a missed seed increases with singulator rate. Secondly, a hole may attract two or more seeds that are sown in close proximity and compete with each other reducing yield. Planters typically contain a scraper to eliminate doubles. When operated at a high rate the scraper may remove both seeds. Thirdly, a hole may become plugged and inoperable. Singulated seeds are conveyed to a furrow by a seed tube or a belt configured to minimize the relative velocity between the seed and ground. Agricultural chemicals may be applied to a proximate secondary furrow.

Seeders are used to deposit typically small cereal grain seeds at densities typically in the range of 25 to 250 seeds per square meter and have a similar top speed of about 15 kph. Seeders known in the art suspend a specified volumetric density of seeds in turbulent airflow and transport the seeds via a network of tubes to outlets proximate to where seed is to be placed. The seeds land in random positions with pre-determined average density. While a seeder is capable of a higher seed rate, seed placement accuracy is lower.

Harvesting machines known in the art collect particles of a bulk crop into a common bin. The average yield and quality for the land area represented by the bin contents can be assessed by the farmer. In current practice, the contents of the harvester bin are transported to progressively larger storage bins as the crop moves from field to on farm storage to elevator. Quality is assessed on the average for the bin, which tends to represent averages over progressively larger land areas. Foreign material and defects may be removed from the crop to improve quality by various means including optical sorters. Optical sorters are known in the art and can provide detailed quality information, but require extensive infrastructure and are limited to fixed sites. U.S. Pat. No. 9,832,928 issued Dec. 5, 2017 propose using sensors to estimate yield as a harvester moves across a field giving a finer grain estimate of how yield varies within a field. The objective of the present invention is to provide detailed quality and yield information in real time on a fine spatial scale and to segregate crop particles into different bins based on quality parameters as a harvester moves across a field.

SUMMARY OF THE INVENTION

According to a first aspect of the invention there is provided a seeding apparatus for applying seeds to a growth medium comprising:
  a storage container for seeds;
  a supply duct for transferring the seeds from the container;
  a singulation device comprising:
    a duct along which the seeds pass;
    an assembly for rotating the duct about an axis such that centrifugal forces generated by the rotation act to drive the seed along the duct and to cause pressure on the seed against a wall of the duct to slide along the wall;
  and a transfer member for transferring the singulated seeds to the growth medium.

The term "seed" used herein is intended to include any material which can be planted and will form growth of a plant from that material. This can of course include cuttings, tubers and root crops such as potatoes.

The term "collected elements" used herein is intended to include any material which is harvested and separated from other crop material. This of course includes seeds or grains but can also include other crop materials or fruits such as berries, grapes and the like.

The term "singulation" used herein preferably relates to a situation where the seeds or elements are separated each from the next with a space between, but this is not essential and in some circumstances the elements may still overlap one with the next or one with a number of others with the separation being enough to obtain meaningful data from observations on the seeds.

The term growth medium can be the soil in a field or a prepared growing bed. The seeding apparatus can move relative to the medium or vice versa.

According to a second aspect of the invention there is provided a seeding apparatus for applying seeds to a growth medium comprising:
- a storage container for seeds;
- a supply duct for transferring the seeds from the container;
- a singulation device for separating the seeds one from the next in a stream;
- a measurement device for detecting one or more parameters of the seeds;
- and a diverting device for extracting some of the seeds so that only selected ones of the seeds are applied in the seeding action.

According to a further aspect of the invention there is provided a seeding apparatus for applying seeds to a growth medium comprising:
- a storage container for seeds;
- a supply duct for transferring the seeds from the container;
- a singulation device for separating the seeds one from the next in a stream;
- a measurement device for detecting one or more characteristics of the seeds;
- and a data storage system for storing data related to the characteristics measured.

According to a further aspect of the invention there is provided a seeding apparatus for applying seeds to a growth medium comprising:
- a storage container for seeds;
- a supply duct for transferring the seeds from the container;
- a singulation device for separating the seeds one from the next such that the spacing between the seeds varies;
- a ground opening device;
- and a transfer member for transferring the singulated seeds to the ground opening device where the transfer device operates at different speeds of transfer.

According to a further aspect of the invention there is provided a seeding apparatus for applying seeds to a growth medium comprising:
- a storage container for seeds;
- a supply duct for transferring the seeds from the container;
- a singulation device for separating the seeds one from the next such that the spacing between the seeds varies
- a ground opening device;
- and a transfer member for transferring the singulated seeds to the ground opening device where the transfer member comprises an intermediate substrate or carrier onto which the singulated seeds are applied where the intermediate substrate is applied to the growth medium and functions to preserve spatial relationships between and among seeds and other particles deposited.

According to a further aspect of the invention there is provided a seeding apparatus for applying seeds to a growth medium comprising:
- a storage container for seeds;
- a supply duct for transferring the seeds from the container;
- a singulation device for separating the seeds one from the next such that the spacing between the seeds varies
- and a transfer member for transferring the singulated seeds to the growth medium;
- wherein there is provided a control device which generates at least two scenarios for plant growth at each location in the growth medium, using a growth model selects the option that best fits user requirements, and issues control signals that cause the seed and related elements to be placed at said location.

According to a further aspect of the invention there is provided a seeding apparatus for applying seeds to a growth medium comprising:
- a storage container for seeds;
- a supply duct for transferring the seeds from the container;
- a singulation device for separating the seeds one from the next in a singulated stream;
- a control device;
- and a transfer member for transferring the singulated seeds to the growth medium;
- wherein the control device selects seeds to be planted at least in part responsive to an input from an external requirement for a particular product, such as a customer request.

According to a further aspect of the invention there is provided a seeding apparatus for applying seeds to a growth medium comprising:
- a storage container for seeds;
- a supply duct for transferring the seeds from the container;
- a singulation device for separating the seeds one from the next in a singulated stream;
- a control device;
- and a transfer member for transferring the singulated seeds to the growth medium;
- wherein there is provided a plurality of seeding devices mounted at spaced positions across the seeding apparatus and wherein each seeding device is associated with a respective one of a plurality of sensing devices each obtaining information relating to conditions of the growth medium at the respective seeding device.

Preferably each sensing device is arranged to obtain information on the growth medium at a location related to a width of a canopy and/or root zone of an individual plant in the crop so that seeding of each plant is associated with information obtained in respect of the individual plant.

In some cases the measurement device which detects one or more parameters of the seeds may only detect the presence of the seeds. In other cases the presence and one or more characteristics of the detected seed may also be obtained.

In accordance with an important optional feature of the invention which can be used independently with any of the above or following features, there is provided a seed measuring device for detecting at least one parameter of the singulated seeds.

In accordance with an important optional feature of the invention which can be used independently with any of the above or following features, there is provided a control system for recording measurements of the seeds relative to time.

In accordance with an important optional feature of the invention which can be used independently with any of the above or following features, there is provided a control system for recording measurements of the seeds relative to location on the ground.

In accordance with an important optional feature of the invention which can be used independently with any of the above or following features, there is provided a control system for providing information about the ground into which the seeds are to be applied and the control system is operable to transfer seeds depending on the information.

In accordance with an important optional feature of the invention which can be used independently with any of the above or following features, there is provided a diverting device for diverting selected seeds away from the ground opening device in response to the detecting of at least one parameter of the singulated seeds.

In accordance with an important optional feature of the invention which can be used independently with any of the above or following features, the singulation rate is higher than a minimum required rate so that a replacement seed is available in instances where a first tested seed does not meet a condition to continue to the transfer device and is discarded.

In accordance with an important optional feature of the invention which can be used independently with any of the above or following features, the storage container for seeds includes at least first and second separate containers containing respective seeds with first and second quality parameters and a control device which selects container is used any time based at least in part on at least one measured parameter.

In accordance with an important optional feature of the invention which can be used independently with any of the above or following features, the singulation device acts to singulate to spacings between the seeds having different lengths and the transfer member operates at timed different timed intervals to change the difference between the spacings either to reduce the difference or to intentionally place the seeds at uneven intervals on the substrate.

In accordance with an important optional feature of the invention which can be used independently with any of the above or following features, the transfer device comprises a belt with receptacles for the seeds wherein the belt is driven at different forwarding speeds to change intervals.

In accordance with an important optional feature of the invention which can be used independently with any of the above or following features, the transfer device is arranged such that the velocity of a seed exiting the transfer device is approximately equal in magnitude and opposite in direction to the relative velocity between the ground opening device and the ground.

In accordance with an important optional feature of the invention which can be used independently with any of the above or following features, the transfer device comprises a funnel and a slot that is operable with an actuator to move between a catch position and a release position. In this arrangement, in some cases there may be provided sensors to detect the presence and/or velocity of the seeds. Another important feature may provide a sensor which detects whether and when the seed actually reaches the ground to ensure accuracy of the seeding action and to halt operation in the event of a blockage or other inconsistent operation.

In accordance with an important optional feature of the invention which can be used independently with any of the above or following features, the seeder includes a system for supplying fertilizer pellets and the number of fertilizer pellets placed or the volume of fertilizer placed per unit length can be varied to bring the concentration of fertilizer at each location to a desired level.

In accordance with an important optional feature of the invention which can be used independently with any of the above or following features, there is provided a rotary body mounted for rotation around an axis with the rotary body defining at least one duct extending from an inner end adjacent the axis outwardly to an outer end spaced at a greater radial distance outwardly from the axis than the inner end, wherein the massed particles are fed at the inner end of said at least one duct, the inner end being arranged in an array adjacent the axis so that the supply conduit acts to deposit the particles at the inner end of said at least one duct for entry of the particles into the inner low velocity end and for separation of the stream of particles in the conduit into separate ones of said at least one duct, said at least one duct being shaped and arranged so that the particles are accelerated as they pass from the inner end to the outer end so as to cause the particles separated into said at least one duct to be aligned one after another in a row in the duct as they move toward the outer end.

In accordance with an important optional feature of the invention which can be used independently with any of the above or following features, there is provided a control system for providing information about the ground into which the seeds are to be applied and the control system is operable to transfer seeds and associated particles to an intermediate substrate depending on the information.

In accordance with an important optional feature of the invention which can be used independently with any of the above or following features, there is provided a control system for providing information about the ground into which the seeds are to be applied and the control system is operable to transfer at least two types of fertilizer that are released at two different rates depending on the information.

In accordance with an important optional feature of the invention which can be used independently with any of the above or following features, the intermediate substrate is applied to the ground or growth substrate so that the intermediate substrate substantially transfers the spatial arrangement of particles on the intermediate substrate to the ground or growth substrate.

In accordance with an important optional feature of the invention which can be used independently with any of the above or following features, the particles to be applied to the intermediate substrate include seeds, chemicals such as fertilizer, herbicides targeting weeds, pesticides or fungicides, biological agents that serve to enhance or protect plants grown from the seeds, or sensor devices.

In accordance with an important optional feature of the invention which can be used independently with any of the above or following features, each region of intermediate substrate is configured to temporally modulate the concentration of fertilizer available to a plant in that region and wherein the temporal concentration profile is chosen at least in part based on a seed placed in the same region.

In accordance with an important optional feature of the invention which can be used independently with any of the above or following features, each region of intermediate substrate is configured to conditionally release fertilizer based at least in part on one or more weather events.

In accordance with an important optional feature of the invention which can be used independently with any of the above or following features, the intermediate substrate comprises an adhesive material that functions to retain a particle.

In accordance with an important optional feature of the invention which can be used independently with any of the above or following features, the singulated seeds are presented to an extruded body as the body is extruded.

In accordance with an important optional feature of the invention which can be used independently with any of the above or following features, a composition of the intermediate substrate is changed at least in part due to at least one measured property of the location where the intermediate substrate is placed.

In accordance with an important optional feature of the invention which can be used independently with any of the above or following features, the intermediate substrate is formed of at least two layers wherein a seed is placed on a first layer and a second layer is subsequently placed to cover the seed.

In accordance with an important optional feature of the invention which can be used independently with any of the above or following features, the intermediate substrate comprises a tube that is braided continuously to enclose the seeds.

In accordance with an important optional feature of the invention which can be used independently with any of the above or following features, the intermediate substrate provides physical protection to the seeds.

In accordance with an important optional feature of the invention which can be used independently with any of the above or following features, the intermediate substrate may further contain a plurality of encoding elements at distinct positions on the intermediate substrate.

In accordance with an important optional feature of the invention which can be used independently with any of the above or following features, the transfer member comprises a placement arrangement which includes a system to translate the seeds in at least two orthogonal directions.

In accordance with an important optional feature of the invention which can be used independently with any of the above or following features, the transfer member comprises a placement arrangement which includes a system to translate the seeds in three orthogonal directions prior to placement on the ground or growth substrate wherein one direction is substantially perpendicular to the ground or growth substrate.

In accordance with an important optional feature of the invention which can be used independently with any of the above or following features, location information is encoded in the pattern of seeds placed on the growth medium.

In accordance with an important optional feature of the invention which can be used independently with any of the above or following features, information about a physical property of each seed in a sequence of seeds placed on the growth medium, is stored along with information about the location the seeds were placed.

In accordance with an important optional feature of the invention which can be used independently with any of the above or following features, the transfer member comprises a measurement system which makes at least one measurement of at least one property and transmits the measurement to a receiver.

In accordance with an important optional feature of the invention which can be used independently with any of the above or following features, the control device includes a sensor which receives at least one measured property of the location.

In accordance with an important optional feature of the invention which can be used independently with any of the above or following features, the growth model of the control device includes information relating to one or more of the following:
  crop property in a prior harvest;
  at least one property of seeds available to the seeder in a seed bin;
  soil condition information at each location;
  predation probability at each location;
  disease probability at each location;
  weed probability at each location;
  elevation of each location;
  air quality at each location;
  weather at each location.

One objective of the current invention is to increase the seed rate so that a field can be planted faster. A further objective of the current invention is to eliminate the need for vacuum and thereby reduce the amount of power required. A further objective of the current invention is to reduce the incidence of errors due to missed seeds and double seeding. A further objective of the invention is to reduce the incidence of faults due to clogging. A further objective of the invention is to provide means to adjust the seed rate so that seeds are sown at desired intervals without overlap. A further objective of the invention is to adjust the seed rate according to measured field conditions. A further objective of the invention is to provide a means to plant a plurality of seed types on the same growth medium and thereby attain an agronomic advantage due to synergy between plants of different types. A further objective of the invention is to provide a means to select crop genotypes well suited to a location. A further objective of the invention is to provide a means for land reclamation and reforestation. A further objective of the invention is to provide information about quality characteristics of the seed sown, the location the seed is sown, the time it is sown, and information about the soil it is sown into.

The invention is a system for placing particles on a substrate comprising a transport means, a reservoir of bulk particles, a singulation means, a particle detection means, an optional measurement means to measure at least one particle parameter, an optional means to measure at least one substrate parameter, a computation means, an optional position sensing means, an optional means to divert the particle to follow at least two different paths based on measured parameters, and a delivery means to convey said singulated particles to the substrate with minimal relative velocity.

The reservoir of bulk particles, singulation means, particle detection means, optional particle measurement means, optional substrate measurement, optional diversion means, optional position sensing means and delivery means is collectively referred to as a singulated particle unit (SPU) hereinafter. The computation means must be in communication with the SPU, whether via directly wired connection or via a wireless link. A plurality of SPU's may be implemented as an array with some elements in common between individual SPU's. In this case it is understood that the logical share of the common element is to be interpreted as the physical element for the purpose of the descriptions below. For example, a reservoir of bulk particles may be common to multiple SPU's, but the description is to be interpreted as if each SPU has a reservoir of bulk particles.

The transport means effects relative motion between the substrate and the SPU. In some embodiments required relative translation between SPU and substrate is obtained by dead reckoning as an offset from a prior relative position. In a preferred embodiment, a position sensing means provides information about the relative position each particle is transferred to the substrate. In a most preferred embodiment, information from a position sensing means is processed to provide signals that guide the transport means to each relative position for particle transfer and provides information about the relative position of the SPU at the instant of particle transfer. In some embodiments, the transport means is a human or animal and the SPU is carried in a backpack or on the animal. In other embodiments the transport means is a tractor and the SPU is either mounted to the tractor directly or mounted on a trailer towed by the tractor. In another embodiment, the transport means is a drone. In another embodiment the transport means is a cable car. In another embodiment the transport means is a cart that runs on rails. In another embodiment the transport means is an XY stage. In another embodiment the transport means is a mobile platform fully or partially immersed in water, to be used for example in aquaculture. In another embodiment the SPU is stationary relative to the earth and the substrate is translated on a conveyor belt or other transfer device. In some embodiments the transport means is controlled by a human operator and in other embodiments the transport means is autonomous: that is the motion is controlled primarily by a computer and sensor system. The growth medium can be located on the conveyor belt or in a pot, sheet or mat or other receptacle moved along the seeding system. In another embodiment, the substrate is carried on a conveyor belt and the SPU is translated relative to the conveyor belt in a direction that is non collinear with the direction of conveyor belt motion. Preferably the SPU is translated in a direction perpendicular to the direction of conveyor belt motion.

In operation, the SPU is translated relative to the substrate by the transport means to a location such that the delivery means is proximate to a location on the substrate where a particle is to be placed at the time of placement in or on the substrate. The required minimum rate of singulation is calculated from the relative speed of the SPU and the desired spacing between particle placement locations on the substrate. Particles are transferred from the reservoir of bulk particles to the singulation means at a rate at least equal to the minimum required rate. The singulation means acts to emit one particle at a time and at least one particle detection means generates a signal that is communicated to the computation means each time a particle is emitted.

The signal duration is the time the particle is within the space measured by the detection means and is proportional to the particle length along the direction of motion. The signal is used within the computation means to increment a singulation counter and to set a starting time for calculating the particle position from the detection means to the exit point of the delivery means by dynamical calculation. At minimum the dynamical calculation requires the starting time, velocity and particle mass together with forces acting on the particle. The velocity can be estimated by measuring the average velocity of a particle immediately after emission from the singulation means in an optional calibration step. A sensor can also be provided which acts to confirm that the seed is released and properly placed.

In another embodiment, the speed of the particle can be measured using the acoustic Doppler effect. In a preferred embodiment the velocity of each particle is measured directly by placing two particle detection means a known distance apart along the particle path and calculating the velocity from the time difference between signals from particle detection means. The particle mass can be an average mass entered as a calibration constant. Preferably, the particle mass can be measured directly for example by a load cell or can be estimated by using the signal duration proportional to particle length in combination with calibration data that relates length and mass. The forces acting on the particle depend on the particular geometry of the SPU and constants such as gravity and coefficients of friction, which are entered into the computation means as empirical constants. It should be noted that the empirical constants such as friction and geometry change with environmental conditions such as temperature and humidity.

In a more preferred embodiment, two additional particle detection means are located proximate to the exit point of the delivery means and provide information about the time and speed of the particle at the point of release. This additional information can be compared with the speed and time predicted by dynamical calculation and used to improve the accuracy of the dynamical calculation by adjusting empirical constants in response to changes in the operating environment.

The computation means calculates when the particle will be within the measurement region of the optional particle measurement means and generates appropriate timing signals to start and stop data acquisition.

In some embodiments the particle measurement means is a spectrometer that provides information about the composition of the particle.

In some embodiments the particle measurement means is an imaging system that provides information about the size, shape and reflectance of the particle at one or more wavelengths.

In some embodiments the particle measurement means is acoustic and provides information about variation in density within the particle.

In some embodiments, a plurality of measurement means is used. In some embodiments, information about the particle together with information about its location on the substrate is stored.

In some embodiments, the particle is a seed and the stored information about seed quality parameters can be correlated with the quality of the plant produced at the stored location. The correlation information can be used to choose the best seed for each location.

In some embodiments, the particle is a fertilizer pellet and information about the pellet composition can be correlated to substrate chemistry at the stored location. The correlation information can be used to choose the best fertilizer for the stored location or used to deliver a custom fertilizer recipe including liquid and powder materials.

In a preferred embodiment, the SPU has a diversion means operable to divert particles to different locations depending upon at least one measured quality parameter of each particle. If a quality parameter meets an operator-determined threshold, the particle continues to the delivery means, otherwise the particle is diverted to a container. For example, if the particle is a seed, a seed determined to be good continues to the delivery means and is planted and a seed determined to be defective is diverted to a reject bin and used for a different purpose. In this embodiment, it is desirable to operate the singulation means at a rate higher than the minimum required rate so that a replacement particle is available shortly thereafter if a particle is diverted away from the delivery means. In some embodiments, surplus particles that are otherwise suitable for placement on the substrate are diverted to a storage bin and re-introduced to the singulation means at a later time. In some embodiments, surplus particles that are otherwise suitable for placement on the substrate are stored in a tube that retains the singulated order for release to the delivery means at a later time.

The optional substrate measurement means transmits information about at least one substrate parameter to the computation means. The substrate measurement means is preferably a spectrometer that provides information about the substrate composition or an imager that provides information about the substrate texture. The substrate measurement means may be acoustic or electromagnetic to provide information about subsurface soil structure. The substrate measurement means may measure the moisture content of soil by for example measuring the dielectric response of the soil. The sampling may be surface sensing or may include sub-surface measurement by a probe or coring device. In a minimal embodiment, information about each substrate location is stored together with information about the particle placed at that location. In the case where the particle is a seed, the quality of the plant produced at the stored location can be correlated with the substrate quality information and used to determine optimal particle placement parameters by location. For example, if the particle is a seed, it may be desirable to place no seed if the substrate is a rock, a lower number of seeds per unit length if the substrate is relatively infertile, and a larger number of seeds per unit length if the substrate has high fertility. For example, if the particle is a fertilizer pellet, the number of pellets placed per unit length can be varied to bring the concentration of fertilizer at each location to a desired level. In a preferred embodiment, a diversion means directs the particle to the delivery means or a bin based at least in part on the at least one measured substrate parameter. In some embodiments, the SPU is associated with a plurality of bulk particle reservoirs, each containing particles with different quality parameters. The computation means selects which one particle reservoir is connected with and feeds the singulation means at any time based at least in part on at least one measured substrate parameter.

An important feature of the invention is that the term "location" in the context of substrate measurements refers to position coordinates typically accurate within a few millimetres and a small area about the position coordinates corresponding to either the root zone or canopy zone of the crop plant which is less than one square meter for most annual crop plants. The substrate properties are preferably measured with a spatial resolution of one meter or less. However, if the substrate is known to be relatively homogeneous and slowly varying, interpolation between measurements made on a coarser scale may be adequate.

In a preferred embodiment the SPU includes a particle measurement means, a substrate measurement means and a particle diversion means. At least one particle parameter and at least one substrate parameter are measured. If the particle parameter meets a condition the particle continues to the delivery means and diverted to a bin otherwise. In a more preferred embodiment, the condition for the particle parameter depends at least in part on the at least one substrate parameter. The at least one particle parameter, at least one substrate parameter and the substrate location where a particle is placed or not placed is stored for subsequent analysis. In some embodiments, the singulation rate is higher than the minimum required rate so that a replacement particle is available in instances where a first tested particle does not meet a condition to continue to the delivery means. In cases where the particle is a seed, this embodiment allows seed quality parameters to be matched with soil quality parameters. That is the best choice of seed for a particular location can be made.

The particle delivery means receives particles from the singulation means with optional measurement and diversion as intermediate steps. The particle delivery means can be a seed tube as is known in the art. The delivery means can be a brush belt as is known in the art. The delivery means can be a foam-covered wheel as is known in the art. These embodiments are configured such that the velocity of a particle exiting the SPU is approximately equal in magnitude and opposite in direction to the relative velocity between the SPU and substrate. That is the relative velocity between the particle and substrate is close to zero. In a preferred embodiment, the delivery means operates to vary the velocity profile of each particle in a manner that causes each particle to be placed closer to a desired location on the substrate. For illustrative purposes, an embodiment based on a brush belt is described in detail.

The brush belt has one region proximate to the singulation means that captures and retains particles and one region proximate to the substrate that releases particles. In prior art, the bush belt moves at a constant velocity between the two positions causing particles that arrive at irregular intervals from the singulation means to be deposited at irregular intervals on the substrate. As the particle rate increases, small differences in the interval between particles become more important. As described previously, the particle time and speed proximate to the singulation means are measured and the dynamics of the particle motion are predicted so that the time a particle arrives at the brush belt can be determined with precision. Further, in this embodiment the brush belt position is measured at the time each particle is captured. For particles to be deposited at equal intervals on the substrate, the brush belt is caused to advance the distance between the last particle deposited and the next closest particle on the brush belt in equal time intervals. As the spacing between particles on the brush belt varies, the speed of the brush belt varies. The brush belt could, for example be driven by a synchronous motor with an encoder or a stepper motor with an encoder. It will be understood that the control mechanism described also enables particles to be placed at intentionally uneven intervals on the substrate in response for example to variations in substrate composition.

In most preferred embodiment, the singulation means is as described in published PCT application WO 2018/018155 by the present applicant published 1 Feb. 2018, the arrangement of which can be used herein and which is incorporated by reference.

The singulation system thus consists of a rotating body with one or more ducts running from a central region where bulk particles are introduced from the bulk particle reservoir to an outer region where singulated particles are released. The particles are accelerated by inertial forces dependent on the angular speed of the rotating body and the shape of the ducts. The singulation rate achieved by a single duct in this apparatus is significantly higher than the singulation rate achieved by vacuum singulation in prior art allowing particles to be placed on a substrate at a significantly higher rate. An agricultural planter based on the present embodiment can traverse a field faster because the singulation step is not rate limiting. Other factors such as the power needed to break the ground or surface roughness may become rate-limiting instead. A singulation system of this type requires only rotary motor which can be conveniently driven by electricity or hydraulic power. The power requirement is a fraction of the power required for a vacuum singulator.

The singulation system described in published PCT application WO 2018/018155 emits particles at intervals determined in part by the distribution of center to center distances in the bulk particles. The average period and variance in the period depend on the size and shape distribution of the particles as well as surface texture, which modulates friction with duct walls. Each particle orients in a duct so as to minimize potential energy. For all but spherical particles, the long axis of the particle will preferentially align with the axis of the duct. The specification includes measurement of particle properties either within a duct or after release as well as a means to redirect particles based on measured properties. The variance in the period between particles causes a corresponding variance in particle positions on the substrate if the particle is transmitted from the singulator unit to a delivery means consisting of a tube. As noted above, using a brush belt as the delivery means and varying the speed of the brush belt can reduce the variance. In some embodiments, a launch angle for a ballistic trajectory to the desired substrate location is calculated and an actuator changes the launch angle to cause the particle to follow the predicted path. In other embodiments, the particle is collected by a funnel and deposited in a slot that is operable with an actuator to move between a catch position and a release position. The width of the slot is selected such that the slot can receive a particle for a length of time corresponding to the variance in release times. After a particle is caught, the actuator accelerates toward the release position and inertial forces drive the particle against the trailing edge of the slot.

In many cases the method includes carrying out an operation on the singulated particles while they remain singulated. That operation can include merely looking at or counting the singulated particles. However the singulation is particularly effective for processing the singulated particles such as by coating, inoculating or sterilizing. In other cases the operation can include carrying out analysis or assessment of the particles.

However in the present application the particles may be used in the singulated state in seeding where the singulation can be carried out at high speed into separate ducts for high speed seeding operations. The singulation can be carried out using a central supply and a single disk with each duct of the disk feeding to separate transfer devices of separate seeding heads. Alternatively each seeding head may include its own singulation device.

While the system can be effective for a single duct to generate a high speed stream of singulated particles, in many cases there is provided a plurality of ducts arranged in an array around the center feed conduit.

The apparatus defined above can be used for detecting at least one measurable parameter of a stream of particles comprising:

carrying particles in a stream of particles in a supply conduit;

rotating a rotary body around an axis;

the rotary body defining at least one duct extending from an inner end adjacent the axis outwardly to an outer end spaced at a greater radial distance outwardly from the axis than the inner end;

the inner end being arranged adjacent the axis so that the supply conduit acts to deposit the particles at the inner end of said at least one duct for entry of the particles into the inner end;

said at least one duct being shaped and arranged so that the particles are accelerated as they pass from the inner end to the outer end so as to cause the particles separated into the duct to be aligned one after another in a row in the duct as they move toward the outer end;

and for each of said at least one duct, measuring said at least one parameter of the particles.

In some cases the apparatus is provided for sorting the particles so that, for each of the ducts, the particles are directed into one of a plurality of paths as determined by the measurement of the parameter. However the measurement of the parameter or parameters, which is obtained more effectively in view of the increased degree of singulation of the particles using the arrangement herein, can be used for other purposes.

The arrangement defined above therefore can provide an advantage that the increased velocity obtained by rotation of the body together with the increased acceleration of the particles on the body better separates each particle from the next for detection of the parameter. In addition the increased velocity of the particles can be used to increase the throughput of the system as the detection or measurement of the parameter can be carried out more quickly.

In one arrangement the measurement of the parameters is carried out while the particles are in the duct. This has the advantage that the location of the particles is more clear and defined since it is controlled by the rotation of the body and the position of the duct. In view of the more accurate location of the particle, the measurement of the parameter can in many cases be carried out more effectively.

In this case preferably the measurement of the parameter is carried out by a measurement device carried on the rotary body. In this way the measurement device is located at a specific position relative to the duct and relative therefore to the particles. This can simplify the operation of the measurement device since it can be focused more accurately on a specific location. In this case each duct may include one or more separate measurement devices dedicated to the measurement of the particles flowing through that duct. That is each particle when moving along a duct can pass a number of sensors or measurement devices, which may be aligned in a row, where each detects a different parameter of the particle to enable a better assessment of the particle to be made. However in some cases a single sensor can provide all of the required information.

Preferably, at least a portion of the duct proximate to the measurement devices is comprised of a transparent material. The provision of a portion of the duct as transparent allows the measurement to be carried out through the transparent section while the duct remains of a constant shape to continue to control movement of the particle.

In one arrangement, the walls of the ducts or the ducts themselves are segmented with one or more gaps between segments. One or more measurement devices are located proximate to the gaps to measure different parameters of the particle with a view unobstructed by the walls of the ducts. Where the duct itself is divided into separated segments, each segment is preferably arranged along the path of the duct substantially parallel to the average velocity vector of the particles at the location of said segment to minimize perturbation of particle flow along the duct. The particle can thus be operated upon using any of the techniques described herein while it is in the gap.

In another arrangement, the separation of the particles can be carried out using electrostatic forces where the particles are charged differentially according to selected parameters and then passed through a field so that the differential charging causes the particles to divert to different paths. Typically, an arrangement is provided which generates an equal charge on each particle so that particles of different mass are separated by passing those particles through an electric field which acts differentially on the particles based on their different masses since each particle has a different or unique charge per unit mass.

Preferably the ducts are curved so that the outer end is angularly retarded relative to the inner end. This shape typically follows closely the path of the particle as it is accelerated under centrifugal force and Coriolis force so that the particle can travel along the path without excessive friction against the sides of the duct.

Preferably the ducts are arranged immediately side by side at the inner ends adjacent the axis so that the feed conduit deposits the particles in the manner which separates the particles directly into the inner ends of the ducts, with the ducts increasing in spacing toward the outer ends as the ducts move toward areas of increased diameter on the rotary body.

Preferably the axis of the rotary body is vertical so that the disk lies in a horizontal plane. However other orientations can be used.

Preferably a side wall of each duct against which the particles run is inclined in a direction along the axis so that acceleration forces on the particles act to move the particles into a common radial plane for release from the rotary body. That is the acceleration forces tend to move the particles axially of the rotary body toward a common axial position. In this way, even if the particles enter the ducts at positions spaced along the axis, the shape of the duct brings them all to the same axial location.

In one preferred arrangement, each duct is shaped such that the acceleration causes the particle to move against a wall of the duct where the wall is V-shaped to confine the particle to a base of the V-shape. The wall can include a surface which includes rifling for engaging and rotating the particle in the duct. In addition the wall can include one or more openings at a location such that components smaller than the particles are separated from the particles by release through openings. Each duct can include an associated second duct parallel to the duct into which the separated smaller components enter. This can be used in a system where there is a stack of such ducts so that the particles are separated by size from the first.

In one example each separating device comprises a separating head having a front edge arranged such that the particles to be separated move toward the front edge in a stream and an actuator for moving the front edge between a first position on one side of the stream arranged to direct the particle to a second side of the stream, and a second position on a second side of the stream, arranged to direct the particle to said one side of the stream.

In this example preferably the separating head is arranged in a radial plane of the rotating body and the first and second sides are arranged on respective sides of the radial plane.

In this example preferably the separating head includes inclined guide surfaces on the first and second sides of the front edge so that the separating head is generally wedge shaped.

Preferably the actuator is moved by piezo electric members. However other drive forces can be used for example an electromagnetic voice coil.

Preferably the actuator is mounted in a tube which extends radially outward of the separating head and lies in a radial plane of the separating head.

The present invention is not limited to the type or size of particle concerned and may be operated with different particles or objects to be separated.

In agriculture, crop yield is optimized by planting a specified number of seeds per unit area. Not all seeds produce viable plants. Extra seeds are planted to compensate for seeds that fail to germinate or fail to produce vigorous plants. The present invention can be used, typically on the seeding or planting apparatus, to sort seeds according to measured parameters related to viability so that seeds most likely to produce viable plants are planted and less viable seeds are used for other purposes. The present invention can be used to sort seeds according to size for compatibility with planting devices. The invention can be used to count seeds so that a specified number can be planted. The present invention can also be used provide a rapid stream of singulated seeds of known quality and number in a planting device. Because the number of singulated seeds per second provided by the present invention is much higher than prior art, a farmer can seed more acres per hour.

While the duct as described in some examples herein is typically a channel with upstanding sides formed in a disk, the duct can also be circular, oval, triangular or quadrilateral etc. or can be a partial tube that is generally C-shaped, V-shaped or L-shaped). The duct can also be defined by a minimal two or three dimensional surface, or surfaces defined by the points of contact imparting force on the particles. The duct can also be an enclosed tube of many different cross-sectional shapes such as circular, oval, triangular or quadrilateral.

The arrangement as described hereinafter may provide the objects to increase the kernel rate, reduce the size of equipment, and reduce the energy requirement.

In some cases the seeding system is configured to apply at least two different types of seed at different locations wherein the type of seed applied depends at least in part on at least one measured parameter from each said location and the at least one measured parameter is chosen from the set of a substrate parameter, a crop plant parameter and a harvested crop element parameter proximate to said location. In some cases the seeding system is arranged to apply associated substances such as fertilizer in or on the ground or substrate. In some cases the seeding system is configured to apply at least two different compositions of associated substances at different locations wherein the composition of associated substances depends at least in part on at least one measured parameter from each said location and the at least one measured parameter is chosen from the set of a substrate parameter, a crop plant parameter and a harvested crop element parameter proximate to said location.

In some embodiments an arrangement to deposit singulated particles from the singulation system on an intermediate substrate or carrier is provided. The intermediate substrate material functions to preserve spatial relationships between and among particles so deposited. The intermediate substrate material may be deposited on the ground or growth substrate at a later second time by a substrate depositing system in a manner that substantially transfers the spatial arrangement of particles on the intermediate substrate to the arrangement of the particles on the ground or growth substrate. For example, if seeds are transferred to an intermediate substrate at an interval of 10 mm, then the intermediate substrate is deposited on the soil in a manner that the interval between seeds is also 10 mm.

In some embodiments the arrangement of particles on a segment of the intermediate substrate of size A is determined at least in part by at least one measured parameter specific to a location on ground or growth substrate of size A and the intermediate substrate segment is transferred to the location. That is, there is a one-to-one mapping between locations on the ground or growth substrate and locations on the intermediate substrate. The particles may be seeds, chemicals such as fertilizer, herbicides targeting weeds, pesticides or fungicides, a sensor device, or biological agents that serve to enhance or protect plants grown from the seeds.

In some embodiments the intermediate substrate completely encloses a seed.

In some embodiments at least one surface of the intermediate substrate is coated with an adhesive material that functions to retain a particle deposited at a location on the intermediate substrate at the location. For example, the intermediate substrate may be a tape with an adhesive on one side that holds seeds brought into contact with the adhesive.

In some embodiments the intermediate substrate is comprised of material that is extruded at the same time as singulated particles are presented to an extruder. For example, a gel with a low bulk modulus is extruded from an extruder continuously and singulated particles impact and become entrained in the gel at controlled intervals. The gel is composed in a manner that the bulk modulus increases shortly after extrusion and incorporation of a particle. The gel modulus may increase for example due to evaporation of a solvent or a change in temperature.

In some embodiments the composition of the extruded gel is changed in a manner that makes the intermediate substrate generated by it more suitable to a particular location wherein the composition is changed at least in part due to at least one measured property of the location where the intermediate substrate will be placed. For example, the concentration of a nutrient dissolved in the gel may be increased when a low concentration of the nutrient is measured at the location where the intermediate substrate is to be placed.

In some embodiments the intermediate substrate is formed of at least two layers wherein a particle is placed on a first layer and a second layer is subsequently placed to cover the particle and first layer. Further, the at least two layers may be fused after the particle is deposited so as to encapsulate the particle.

In some embodiments the intermediate substrate is comprised of a fibre tube that is braided continuously and about each particle as it is introduced from the singulation system. Further the diameter of the fibre tube may vary in a manner that constrains each particle to a short segment of the fibre tube.

In some embodiments the intermediate substrate carries a single seed. In some embodiments the intermediate substrate carries a plurality of seeds.

In some embodiments the intermediate substrate is composed of a rigid leading section and a payload section. Preferably the leading section is shaped as a spike to penetrate the ground or growth medium. Preferably the leading section is biodegradable. In some embodiments the leading section contains at least one of fertilizer, herbicide, fungicide, pesticide, or a biological agent to aid plant growth. In some embodiments the payload section is enclosed with a rigid casing attached to the leading section that is left in the ground or growth medium after placement. In some embodiments the payload section is enclosed in a tube integral to the substrate placement means wherein said tube attaches to leading section during intermediate substrate placement and detaches after intermediate substrate placement leaving said leading section and payload section in ground or growth substrate. In a preferred embodiment a portion of the payload section contains a seed. Preferably the diameter of the payload section is at least twice the seed diameter. In some embodiments, a portion of the payload section further contains soil in contact with seed. In some embodiments a portion of the payload section contains a transport regulating medium that regulates the transport rate of a chemical substance such as fertilizer to the seed. In some embodiments a portion of the payload section contains fertilizer. In some embodiments a portion of the payload section contains fungicide for inhibiting fungal infection. In some embodiments a portion of the payload section contains pesticide for inhibiting insects. In some embodiments a portion of the payload section contains herbicide for inhibiting weeds. In some embodiments a portion of the payload section contains a biological agent that promotes plant growth.

In some embodiments the particles are attached to the intermediate substrate on the rotating singulation system. In other embodiments the particles are attached to the intermediate substrate after singulated particles leave the rotating singulation system.

In some embodiments the intermediate substrate contains fertilizer in regions proximate to a seed location and is structured to release the fertilizer to the plant growing from the seed in a controlled manner. The intermediate substrate may have, for example a composition that regulates the rate of diffusion of fertilizer from one or more reservoirs to the plant.

In some embodiments, the intermediate substrate is composed in a manner that inhibits the diffusion of fertilizer out of the substrate layer and allows diffusion of fertilizer in a controlled manner to a plant growing from a seed placed on or in the substrate. The intermediate substrate may have for example a layered structure wherein the inner layers allow diffusion of fertilizer and outer layers block diffusion of fertilizer.

In some embodiments the intermediate substrate is composed in a manner that provides physical protection to the seeds. For example the intermediate substrate may contain material that an insect cannot chew through.

In some embodiments information about at least one measurable physical property of each seed in a sequence of seeds placed on a growth substrate, an intermediate substrate, or the ground is stored in a database or other format along with information about the location the seeds were placed.

In some embodiments a measurement system is added to at least one location on the intermediate substrate and the measurement system makes at least one measurement of at least one property and transmits the measurement to a receiver. The measured property can be the concentration of a chemical substance such as water, chemicals essential for plant growth and health such as but not limited to compounds containing nitrogen, phosphorous, potassium, calcium, iron, and selenium, or a gas such as carbon dioxide, methane or oxygen. The measured property can be temperature. The measured property can be light. The measured property can be vibration indicating for example the presence of an insect. The measured property can be the presence of a biological agent such as a fungus by for example opening a gate causing a micro-fluidic ELISA analysis chip to sample the environment around the substrate at a pre-set or triggered time.

In some embodiments the intermediate substrate may further contain a plurality of encoding elements at distinct positions on the intermediate substrate. The encoding elements may consist of a plurality of zones that are physically or chemically distinct from the intermediate substrate. Physically distinct zones can for example be perforations, indentations, scratches, variations in texture, variations in magnetic orientation, variations in electronic orientation, variations in optical axes and the like. Chemically distinct zones may for example be ink marks forming a bar code, a pattern of dots or a sequence of symbols. The encoding elements may be a transponder such as a RFID tag. The encoding elements may be positioned at the end points of a segment of intermediate substrate containing a sequence of particles such as seed and/or fertilizer between the end points. The encoding elements may specify a key in a database and the key is used to identify the location on the ground or growth substrate that point where the intermediate substrate is to be placed. Two encoding elements are sufficient to specify the placement of a linear segment of intermediate substrate and three encoding elements are sufficient to specify the placement of a planar segment of intermediate substrate. For example the end points A and B identified by encoding elements on a segment of intermediate substrate may correspond to points A' and B' on the ground or growth medium. More encoding elements may be included in a segment of intermediate substrate that are redundant and may be used to correct errors reading the encoding elements due to, for example dust in a field. In some embodiments an encoding element is associated with each seed or particle. The location on the intermediate substrate can be specified by the encoding elements to a precision of a millimetre or better.

In some embodiments a substrate placement arrangement includes a system to translate the intermediate substrate in three orthogonal directions prior to placement on the ground or growth substrate wherein one direction is substantially perpendicular to the ground or growth substrate. For example the placement arrangement may include an XYZ stage including a stepper motor for each direction of travel. In the case that the seeder apparatus as a whole is translated in direction X relative to the ground, the placement arrangement may include linear displacement stage oriented in direction Y, where direction Y is different from direction X and a linear displacement stage oriented in direction Z substantially perpendicular to the ground. Preferably direction Y is orthogonal to direction X. In a preferred embodiment, the intermediate substrate placement means includes a stage that translates with a velocity equal and opposite to the velocity of the seeder apparatus such that the velocity of the intermediate substrate placement means is zero with respect to the ground during placement of at least a portion of said intermediate substrate. In some embodiments the substrate placement means may have a precision of a millimetre or better.

In some embodiments the substrate placement arrangement is linked with a location determining system which operates to measure the location of a reference point on the seeder apparatus relative to the earth. The location determining system may for example be a GPS receiver. The location determining system may for example be a radio receiver that receives signals from beacons placed at reference points on a field. The location determining system may be an optical device that emits an optical pulse and measures the time of flight or phase of the pulse reflected from a reference point. Those skilled in the art will recognize that the uncertainty in these measurements may be much greater than the precision of either the substrate placement system or the placement of seeds on the intermediate substrate. For example, the uncertainty in a single GPS measurement may be about 1000 mm whereas the precision of seed placement on the intermediate substrate can be about 1 mm. In order to achieve millimetre seed placement precision on a field, GPS location information alone is not enough. Other location measurement means are needed to supplement or replace GPS.

According to a further aspect of the invention there is provided a method for growing crops in a growth medium comprising:
  seeding the growth medium with seeds for the crops;
  harvesting the crops and separating collected elements of the crops from other crop material;
  during the seeding, placing said seeds in different patterns in the growth medium where the patterns define respective different locations in the growth medium;
  and subsequent to seeding identifying said different locations by reading the different patterns.

In some embodiments, location information is encoded in the sequence of seeds placed on the ground, placed on a growth substrate, or placed on an intermediate substrate. The location information may be encoded by both the relative positions of seeds and by the types of seed. In some embodiments location information is encoded in the spacing between seeds placed on the ground, placed on a growth substrate, or placed in an intermediate substrate. In some embodiments location information is encoded as a series of different displacements between seeds along a longitudinal axis. In some embodiments location information is encoded as a series of different seed displacements transverse to a longitudinal axis. In some embodiments location information is encoded in a combination of seed type sequence and inter-seed displacement. In some embodiments a location means provides accurate position information with more precision than displacements between seeds and seed placement positions are referenced to accurate absolute coordinates. In some embodiments a location means is less precise than inter-seed displacements and seed placements are referenced to a relative displacement to a preceding seed location or locations. While it may not be feasible to measure the position or type of seed after placement in the ground directly, the location information can be read after the seeds sprout by the location and type of plants that grow from the seeds. For example, a GPS location may be used to identify a region of plants grown from a known pattern of seeds. The position of each plant can be measured and the positions can be compared with the positions of the known pattern of seeds to find the closest match. Once the pattern of plant positions is matched with the pattern of seed positions, each plant can be matched with the seed that produced it. In the case that two or more types of seed are planted, the location can be inferred by the plant type. For example, if barley B and canola C seeds are placed in the sequence BBBCBCCB, then the location can be determined by searching for the sequence BBBCBCCB in the region specified by a lower resolution location determining device. The identity of the seed that produced each plant in the sequence can be determined once the sequence is matched. Further, the identity of the seed that produced each plant in adjacent regions can be identified merely by counting the number of plants in the sequence relative to the known reference sequence. The code sequence in the example above is equivalent to an eight bit number that can be used to identify one of 256 reference locations. The effective number of bits can be increased by any combination of increasing the length of the sequence, increasing the number of types of plant, and by including relative position information as discussed above.

In some embodiments a single type of seeds is planted generally in a line along a first axis and location information is encoded as a sequence of displacements between successive seeds along said first axis. For example, the sequence of displacements may form a longitudinal seed density waveform along said first axis. For example, the sequence of displacements may be transverse to said first axis to form a transverse waveform. The waveform may consist of both longitudinal and transverse displacements. The waveform consists of at least three and preferably more than fifteen consecutive seed positions. A longer sequence of seed positions is preferred because the waveform can be read even if some of the seeds fail to germinate and contribute to the location information. Indeed, once the waveform is determined, the identity of seeds that failed to germinate can be determined by a void at their expected positions. In some embodiments two-dimensional location information is encoded by varying either the phase or waveform of successive lines parallel to first axis and transversely displaced.

In some embodiments a computation means generates at least two scenarios for plant growth at each location on a field or growth substrate, selects the option that best fits user requirements, and issues control signals that cause the seed and related elements to be placed at said location.

In some embodiments the computation means receives location information from a location measuring means and at least one measured property of the location from a sensor means, and generates at least two scenarios for plant growth based at least in part on the at least one measured property at measured location, selects the option that best fits user requirements, and issues control signals that cause the seed and related elements to be placed at said location.

In some embodiments the computation means receives information about one or more crop properties in a prior harvest at each location and generates at least two scenarios for plant growth based at least in part on said prior harvest information at each location on a field or growth substrate, selects the option that best fits user requirements, and issues control signals that cause the seed and related elements to be placed at said location.

In some embodiments the computation means receives information about at least one property of seeds available to the seeder in a seed bin and generates at least two scenarios for plant growth based at least in part on said seed property, selects the option that best fits user requirements, and issues control signals that cause the seed and related elements to be placed at said location.

In some embodiments the computation means receives information about location and at least one seed property from a sensor measuring a singulated seed immediately available at said location and generates at least two scenarios for plant growth based at least in part on said seed property and said location, selects the option that best fits user requirements, and issues control signals that cause the seed and related elements to be placed at said location.

In some embodiments the computation means receives information about soil conditions at each location from prior measurements and generates at least two scenarios for plant growth based at least in part on said soil condition information at each location on a field or growth substrate, selects the option that best fits user requirements, and issues control signals that cause the seed and related elements to be placed at said location.

In some embodiments the computation means receives information about the elevation of each location and generates at least two scenarios for plant growth based at least in part on said elevation information at each location on a field or growth substrate, selects the option that best fits user requirements, and issues control signals that cause the seed and related elements to be placed at said location.

In some embodiments the computation means receives information about past weather at each location and generates at least two scenarios for plant growth based at least in part on said weather information at each location on a field or growth substrate, selects the option that best fits user requirements, and issues control signals that cause the seed and related elements to be placed at said location.

In some embodiments the computation means receives information about location, elevation, soil conditions, past weather, prior harvest yield, and seed properties, generates at least two scenarios for plant growth based upon at least in part on at least some of the said inputs, selects the option that best fits user requirements, and issues control signals that cause the seed and related elements to be placed at said location.

According to a first aspect of the invention there is provided harvesting machine comprising:

a harvesting system including components for collecting elements to be harvested from crops in a growth medium and for separating the collected elements from other crop material;

a transport arrangement for causing relative movement between the growth medium and the harvesting system;

a separating system for separating some of the collected elements from others of the collected elements;

the separating system including a sensing system arranged to measure at least one property of the collected elements wherein the elements are separated based on the property sensed.

It will be appreciated that the harvester may be mounted on or attached to a tractor for movement across a field or the crops may be mounted in a travelling transport system past a stationary harvesting system.

In accordance with one important feature of the invention there is provided a sensing system including a processor arranged to measure at least one property of each separate element wherein the elements are separated based on the property sensed.

According to a second aspect of the invention there is provided harvesting machine comprising:

a harvesting system including components for collecting elements to be harvested from crops in a growth medium and for separating the collected elements from other crop material;

a transport arrangement for causing relative movement between the growth medium and the harvesting system;

a separating system for separating some of the collected elements from others of the collected elements;

wherein there is provided an auxiliary harvesting unit to harvest separately collected elements from a selected plant or area.

The arrangement herein can be used for harvesting crop seeds and separating the seeds from other crop material where, in advance of the harvesting, analyzing the crop to determine selected plants or areas of plants, separately from the harvesting of the seeds, using an auxiliary harvesting device to harvest the selected plants or areas of plants to form a supply of selected seeds and seeding using at least some of the selected seeds.

Preferably the seeding occurs using location data which can include data obtained in the harvesting and sorting process to determine the growth potential of certain areas of a field.

In accordance with an important optional feature of the invention which can be used independently with any of the above or following features, the auxiliary harvesting unit is mounted on the transport arrangement for movement relative to the harvesting system to a required location.

In some cases the collected elements are separated on a common machine with the harvesting. However optionally, the collected elements can transported to a site separate from a harvesting machine and are separated at the separate site.

According to a further important aspect of the invention, during planting, crops are placed at set locations in a pattern related to different locations in the growth medium and during the harvesting detecting the pattern in the crops and determining the location on the substrate by analyzing the pattern.

The pattern or coding can be one dimensional in either the transverse or longitudinal direction or can be two dimensional in both the transverse and longitudinal direction to determine a specific location in the substrate.

In one arrangement, the pattern can be detected by measuring the harvested crops elements after harvesting while on the harvesting machine by analyzing the seeds or crop elements. This may provide only a relatively coarse location on the substrate requiring bands of the individual crops to be planted. However alternatively or in addition the pattern can be detected by measuring the crops in advance of the harvesting using various forms of machine mounted or separate sensors.

In accordance with an important feature of the invention which can be used independently with any of the above or following features, there is provided a mechanical sorting device responsive to the sensing system for directing the elements into separate paths.

In accordance with an important optional feature of the invention which can be used independently with any of the above or following features, the paths are directed to separate storage containers carried on the transport arrangement. However the storage may occur on another component of the system.

In accordance with an important optional feature of the invention which can be used independently with any of the above or following features, there is provided a device for separating the elements into a singulated stream of the elements for the measurement.

In accordance with an important optional feature of the invention which can be used independently with any of the above or following features, the sensing system comprises any device that receives a particle flux from the crop particle to be measured and can perform the measurement step which may include photons, electrons, neutrons, atoms, ions, molecules, or any combination of the aforesaid.

In accordance with an important optional feature of the invention which can be used independently with any of the above or following features, the sensing system operates to obtain Information about at least one quality parameter of each crop particle which is analyzed to provide a classification of the element.

In accordance with an important optional feature of the invention which can be used independently with any of the above or following features, the sensing system operates to obtain the time the particle is processed.

In accordance with an important optional feature of the invention which can be used independently with any of the above or following features, the sensing system operates to generate summary statistics of the sensed elements and optionally the separation and the time.

In accordance with an important optional feature of the invention which can be used independently with any of the above or following features, the sensing system processor operates to obtain a location of the harvesting system during the sensing.

In accordance with an important optional feature of the invention which can be used independently with any of the above or following features, the method includes separating some of the elements from others based on a location of the crop. That is the system can detect the location of the harvesting system relative to the crop and can select certain seeds or elements based on that location and can store or use them independently. This can be used in conjunction with an additional sensing system configured to detect phenotype parameters of crop plants in advance to the harvesting system. Those selected plants can then be harvested separately and the elements from the auxiliary harvesting unit can be stored in relation to information relating to a location of the plant or area. The sensors which detect the crop can be mounted on the harvester on an upfront mechanical support or at other locations. Alternatively the harvester can use information obtained from sensors mounted on other platforms. Other platforms may include other harvester units, a survey vehicle, drones and satellites.

In accordance with an important optional feature of the invention which can be used independently with any of the above or following features, the sensing system processor is arranged to generate statistics about how parameters of the elements relate spatially as the harvesting system moves from location to location.

In accordance with an important optional feature of the invention which can be used independently with any of the above or following features, the statistics are used to allocate land to crop varieties and plan fertilizer inputs for subsequent crops.

In accordance with an important optional feature of the invention which can be used independently with any of the above or following features, the sensing system includes an input arranged to change the sort classification criteria.

In accordance with an important optional feature of the invention which can be used independently with any of the above or following features, the processor includes an input by which end users communicate their quality requirements and the sensing system processor is arranged to place elements in separate paths dedicated to the requirements of the end user.

In accordance with an important optional feature of the invention which can be used independently with any of the above or following features, the quality characteristics determined by the sensing system are used to market the crop and increase its aggregate value.

In accordance with an important optional feature of the invention which can be used independently with any of the above or following features, there is provided an additional sensing system configured to detect phenotype parameters of crop plants on the ground in advance to the harvesting system.

In accordance with an important optional feature of the invention which can be used independently with any of the above or following features, the processor or a central control system is arranged to carry out a statistical analysis to produce information about how yield and quality parameters correlate with seed parameters as a function of location to enable a farmer to plant the best type of seed for each location in a field.

In accordance with an important optional feature of the invention which can be used independently with any of the above or following features, there is provided an auxiliary harvesting unit in advance of the harvesting system to harvest separately elements from a selected plant or area.

The auxiliary harvesting unit can be mounted on the transport arrangement for movement across the harvesting system to a required location or it can be a system in advance of the conventional header which includes an array of picking components across the header to operate on selected plants leaving other plants to be harvested conventionally. Alternatively the auxiliary system can be an entirely separate independent system carried and operated independently. The analysis necessary to determine the plants to be harvested can be carried out optically for example by image analysis or by other methods available to person skilled in this art. The analysis can use sensors on the harvester or other independent sensors.

Preferably the elements from the auxiliary harvesting unit are themselves measured and sorted in order to select the best in relation to certain selected characteristics from the total. The best of those could be used in a seeding system or retained for other purposes.

In accordance with an important optional feature of the invention which can be used independently with any of the above or following features, there is provided a seeding system attached to the transport arrangement for applying seeds to the ground or substrate after the harvesting. In some cases the seeding system is configured to apply at least two different types of seed at different locations wherein the type of seed applied depends at least in part on at least one measured parameter from each said location and the at least one measured parameter is chosen from the set of a substrate parameter, a crop plant parameter and a harvested crop element parameter proximate to said location. In some cases the seeding system is arranged to apply associated substances such as fertilizer in or on the ground or substrate. In some cases the seeding system is configured to apply at least two different compositions of associated substances at different locations wherein the composition of associated substances depends at least in part on at least one measured parameter from each said location and the at least one measured parameter is chosen from the set of a substrate parameter, a crop plant parameter and a harvested crop element parameter proximate to said location.

In accordance with an important optional feature of the invention which can be used independently with any of the above or following features, the seeding system receives selected elements from the sorting device.

In accordance with an important optional feature of the invention which can be used independently with any of the above or following features, the type of seed sown by the seeding system together with its location is stored.

At minimum, the invention comprises a transport means, a harvesting means, a mechanical sorting means that acts on each item, and a plurality of storage means. The system as a whole comprising a transport means, a harvesting means, a sorting means, a plurality of storage means, and optional features is referred to hereinafter as a harvest sort system abbreviated HSS. The transport means is any vehicle that moves the harvest means, sorting means, and storage means from one location to another. The harvesting means refers to one or more pieces of equipment that perform the functions of removing at least a portion of a crop plant from its growth location, processing said portion to separate usable parts and unusable parts, and transferring usable parts to a storage means.

The term 'sorting means' refers to a mechanical system that separates a collection of particles into individual particles, measures at least one property of each particle, and directs each particle to a destination based at least in part on the at least one measured property. Storage means refers to any enclosure that at least partly constrains the movement of a plurality of particles. Normally, storage means refers to a bin, but a short section of pipe (normally used to transfer particles from one location to another) can also constitute storage means for the purpose of the invention.

While the separation step typically acts to separate the particles in to individual elements which are sufficiently separate to allow the individual parameters of the particle to be measured, in some cases the same system can be used where the particles are only sufficiently separated to obtain meaningful measurements of a group of particles. That is the particles may be formed into a stream where the particle are partly overlapped and the measurement may be an average of two or more particles rather than obtained from a single particle.

In another embodiment, the sorting means and storage means may be small enough to be carried by a human or may instead be carried on a cart. The cart may be motorized, pulled by a human, or pulled by an animal. In a preferred embodiment, the mechanical harvesting means and mechanical sorting means are carried together with a storage means on a mechanical transport means particularly a combine harvester. In simple terms, the preferred embodiment has the features of a combine plus the added feature of sorting means.

In a preferred embodiment, the sorting means comprises a singulation step, a measurement step, and a diversion step. In a most preferred embodiment, the singulation step and diversion steps are performed as described in published PCT application WO 2018/018155 by the present applicant published 1 Feb. 2018, the arrangement of which can be used herein and which is incorporated by reference.

This document discloses a singulator which consists of a rotating body with one or more ducts running from a central region where bulk particles are introduced to an outer region where singulated particles are released. The particles are accelerated by inertial forces dependent on the angular speed of the rotating body and the shape of the ducts. Inertial force also orients particles so as to minimize potential energy. For all but spherical particles, the long axis of the particle will preferentially align with the axis of the duct. The specification includes measurement of particle properties either within a duct or after release as well as a means to redirect particles based on measured properties. Any device that receives a particle flux from the crop particle to be measured and can perform the measurement step. The particle flux may be photons, electrons, neutrons, atoms, ions, molecules, or any combination of the aforesaid. In some embodiments the measurement step is performed using light scattering as described in U.S. Pat. No. 8,227,719 (Prystupa et al) issued Jul. 24, 2012, the disclosure of which is incorporated herein by reference and can be studied for further information.

In other embodiments the measurement step can be performed by a spectrometer chosen from the group of x-ray, UV-Vis, near infrared, mid infrared and Raman that analyses the chemical composition of a particle. In other embodiments, the measurement step is performed with a mass spectrometer.

In another embodiment the simple mass can be measured using a load cell.

In another embodiment, the measurement means uses acoustic waves to measure soundness and detect voids. In another embodiment, the measurement means is a multi-spectral camera that analyzes the size, shape and surface features of a particle. In another embodiment, the measurement means is capacitive to measure the dielectric constant and moisture content of the particle. In a more preferred embodiment, at least two measurement means listed are used. In an even more preferred embodiment, at least three of the measurement means listed are used. Information about at least one quality parameter of each crop particle is analyzed to provide a classification of the each crop particle and the crop particle is diverted to a storage bin corresponding to the classification. For example, if the crop particle is a barley kernel, the barley kernel can be classified as fit for malting, fit for feed or diseased. Barley kernels fit for malting are diverted by the sorter to a malting bin, barley kernels fit for feed are diverted to a feed bin, and diseased barley kernels are diverted to a recycle bin.

In another embodiment, the system herein comprises a transport means, a harvesting means, a sorting means, a plurality of storage means, a computation means and a presentation means. The computation means described here is incremental to the functionality described above within the scope of the sorting means and may be performed on the same computing device. The computing means receives information about the measured parameters of each crop particle and the classification assigned to each crop particle together with the time the particle was processed from the sorting means and generates summary statistics. The summary statistics may include but not limited to the number of crop particles processed, the total mass, statistics describing the mass distribution, the number of crop particles processed per unit time, the number of crop particles in each classification, the number of crop particles in each classification processed per unit time, and aggregate quality statistics for each classification. The quality parameters may include, but are not limited to size, shape, mass, granule size, disease such as the presence of fungus, presence of presence of mycotoxins, predation such as the presence of insects, presence of herbicide, presence of pesticide, moisture content, total protein, protein types, amino acid profile, total carbohydrates, amylose/amylopectin ratio, lipids, flavenoids, and elemental analysis including isotopes. In a more preferred embodiment, the HSS comprises all the prior elements plus a means to measure the location of the harvester means.

The location information may be derived from GPS or from dedicated position transponders or from analysis of crop plant patterns, or from any combination thereof. The computation means generates statistics about how crop particle parameters relate spatially as the HSS moves from location to location.

The location can be carried out using the crop coding of two or more crops described hereinafter where the different crops are laid out in a pattern which defines a measurable code to identify a unique location.

The computation means transmits at least some of the statistics generated to a presentation means. The presentation means can be for example a display screen. The information may be presented in graphical form for the operator to make immediate decisions about both harvesting and sorting. The operator may elect to change sort classification criteria part way through a harvest in order to optimize the aggregate value of the crop. The information may be used to allocate land to crop varieties and plan fertilizer inputs for subsequent crops in the same year or subsequent years. Most importantly, detailed information about the quality characteristics can be used to market the crop and increase its aggregate value. Since the sorting and classification is done during the harvest process, the crop is available for immediate delivery.

The presentation means may present information from multiple harvesters running side by side or even at geographically different locations and a master operator can coordinate the operation of the harvesters to collect and aggregate amounts of desired crop bins across multiple locations.

In a more preferred embodiment, the arrangement herein includes all of the preceding features plus a means for end users to communicate their quality requirements to the harvesting system and for the harvesting system to place crop particles in separate bins dedicated to each end user. The harvesting system further communicates to each end user the volume of crop particles collected in the dedicated bin that met their quality requirements. Crop particles not assigned to an end user are placed in bins assigned by the operator usually, but not necessarily corresponding to established commodity grades.

In a more preferred embodiment, the invention includes all of the preceding features plus one or more sensors configured to detect phenotype parameters of crop plants prior to the harvesting operation. The plant sensors are preferably hyperspectral cameras operable from 600 nm to 1700 nm or more preferably from 400 nm to 2300 nm with 10 nm or better spectral resolution. Cameras operable over limited wavelength ranges or even monochrome cameras are within the scope of the invention, but less preferred.

The additional sensors may be mounted on the harvesting system or on an independent vehicle such as a drone. The additional sensors convey information about phenotype parameters and location of individual crop plants or groups of crop plants within a small region to the harvesting system. The harvesting system of the present invention takes the additional step of relating the plant phenotype information to the crop particle information obtained in the sorting step to produce information about how plant phenotypes correlate with crop particle quality characteristics. It should be noted that the phenotypes and crop particles may be from different types of crop plants: that is the properties of different types of crop plants may be correlated. In this way, hyperspectral data from a known location can be correlated with quality data from the harvested crop to better model the harvest quality based on hyperspectral imaging. The information obtained can be used to identify the effects of competition and mutualism between plants and thereby improve agronomic models used to predict crop growth. In some embodiments, the improved agronomic models may be specific to a particular location or set of locations in a field wherein the size of a location is the size of the canopy or root zone of a crop plant, typically less than one square meter. In other embodiments the improved agronomic model may be based on information about crop phenotypes, crop particle properties, substrate properties and weather from multiple locations on multiple fields from sensors on multiple harvesters. The model can be used subsequently to optimize the harvest timing based on hyperspectral surveys of field conditions. As phenotype parameters change with time (plant maturation), detailed information about how phenotypes correlate with seed quality in the harvest enables an operator to choose a harvest time that optimizes the aggregate quality of harvested seeds. It should be noted that quality characteristics of one crop type may correlate with quality characteristics of a different crop type, so information about the harvested crop type can be used to predict the performance of a different crop type. The information also enables the operator to identify phenotypes associated with desirable quality characteristics for each region of a crop area and to seed the best performing cultivars for each location in subsequent crops. This information allows the operator to preferentially bin seeds from desirable phenotypes separately and to plant those seeds for future crops.

In some cases the additional sensors can be used in advance of the harvesting to locate or mark individual plants or areas of plants which can then be harvested individually. The marking can be carried out to mark the plant itself and/or to mark the seeds or components to be harvested from the plants. When the plant is marked, the harvesting can be carried out to harvest the marked plants separately. This can be done using the auxiliary harvester described herein. Where the seeds themselves are marked the plant elements or seeds from the marked plants can be separated by the sorting system on the harvester by detection of the marking during the singulation and sorting.

The above data can also be correlated with soil sampling carried out on the harvester or separately on the remote sensors. The sampling may be surface sensing or may include sub-surface measurement by a probe or coring device. The system can operate to analyze samples of the soil itself both when seeding and harvesting.

In a more preferred embodiment, the invention includes all of the preceding features plus a storage medium containing information about the locations and quality characteristics of seeds sown in the field to be harvested. The phenotypic information obtained at each harvest location together with seed quality information for that location is analyzed with multivariate statistical analysis to produce information about how yield and quality parameters correlate with seed parameters as a function of location. This information would enable a farmer to plant the best type of seed for each location in a field.

In a more preferred embodiment, the invention includes all of the preceding features plus an auxiliary harvester designed and configured to harvest selected individual plants before remaining plants in the harvest system's path are harvested by the primary harvesting means. In an example embodiment, the primary harvesting means is a combine and an auxiliary-harvesting unit is mounted to run on a rail perpendicular to the combine's direction of travel and ahead of the main cutting head. Depending on the width of the combine, more than one auxiliary harvesting units may be required to traverse the distance to a selected plant within an acceptable response time. In this embodiment, plants with desirable phenotypes and desirable seed quality parameters are individually selected by analysis of information from the crop sensors. Information about the location of the plant is relayed to an auxiliary-harvesting unit, which moves to the selected plant location and extracts crop particles (usually seeds). The crop particles are conveyed from the auxiliary-harvesting unit to a dedicated sorting unit, which sorts the crop particles according to at least one measured quality parameter and forwards the crop particles to a storage bin based at least in part on the measured quality parameter(s). This embodiment is particularly useful for phenotypic plant breeding and selection of seed stock adapted for a particular location. The present invention automates the process of selecting germ seed for new cultivars specifically adapted to the soil and micro-climate of a particular location. Simultaneous selection for multiple factors including but not limited to disease resistance, lodging resistance, drought resistance, flood resistance, frost resistance, insect resistance, herbicide tolerance, yield and quality parameters enumerated above is possible with the present invention.

In some embodiments the HSS includes planter means. The planter means functions to place seed and possibly associated substances such as fertilizer in or on the ground. In some embodiments the planter means further receives seed from the sorter means. That is seed is harvested, sorted and planted in a single pass. The planter means follows the harvester means so both seeding and harvesting can be done in a single pass, saving time. In a preferred embodiment at least one planter parameter is determined at least in part by at least one measured parameter of crop particles and/or at least one measured parameter of crop plants. In a more preferred embodiment, the at least one planter parameter is adjusted dynamically in response to changes in the at least one measured parameter of crop particles or at least one measured parameter of crop plants. In a preferred embodiment information about the type of seed sown by the planter means together with its location is stored. The composition of crop plants and particles depends on local factors including microclimate and soil conditions and hence provide an indirect measure of both that can be extracted by statistical methods.

In accordance with an important optional feature of the invention which can be used independently with any of the above or following features, the seeds or elements can be separated using a method for singulating particles comprising:

providing a supply of massed particles in a supply conduit;

rotating a rotary body around an axis;

the rotary body defining at least one duct extending from an inner end adjacent the axis outwardly to an outer end spaced at a greater radial distance outwardly from the axis than the inner end;

feeding the massed particles at the inner end of said at least one duct;

the inner end being arranged in an array adjacent the axis so that the supply conduit acts to deposit the particles at the inner end of said at least one duct for entry of the particles into the inner low velocity end and for separation of the stream of particles in the conduit into separate ones of said at least one duct;

said at least one duct being shaped and arranged so that the particles are accelerated as they pass from the inner end to the outer end so as to cause the particles separated into said at least one duct to be aligned one after another in a row in the duct as they move toward the outer end.

In many cases the method includes carrying out an operation on the singulated particles while they remain singulated. That operation can include merely measuring or counting the singulated particles. However the singulation is particularly effective for processing the singulated particles such as by coating, inoculating, sterilizing. In other cases the operation can include carrying out analysis or assessment of the particles. However in other cases the particles may be used in the singulated state such as in the seeding methods described above where the singulation can be carried out at high speed into separate ducts for high speed seeding operations.

While the system can be effective for a single duct to generate a high speed stream of singulated particles, in many cases there is provided a plurality of ducts arranged in an array around the center feed conduit.

In accordance with an important optional feature of the invention which can be used independently with any of the above or following features, the method for detecting at least one measurable parameter of a stream of particles comprises:

carrying particles in a stream of particles in a supply conduit;

rotating a rotary body around an axis;

the rotary body defining at least one duct extending from an inner end adjacent the axis outwardly to an outer end spaced at a greater radial distance outwardly from the axis than the inner end;

the inner end being arranged adjacent the axis so that the supply conduit acts to deposit the particles at the inner end of said at least one duct for entry of the particles into the inner end;

said at least one duct being shaped and arranged so that the particles are accelerated as they pass from the inner end to the outer end so as to cause the particles separated into the duct to be aligned one after another in a row in the duct as they move toward the outer end;

and for each of said at least one duct, measuring said at least one parameter of the particles.

In some cases the method is provided for sorting the particles so that, for each of the ducts, the particles are directed into one of a plurality of paths as determined by the measurement of the parameter. However the measurement of the parameter or parameters, which is obtained more effectively in view of the increased degree of singulation of the particles using the arrangement herein, can be used for other purposes.

The arrangement defined above therefore can provide an advantage that the increased velocity obtained by rotation of the body together with the increased acceleration of the particles on the body better separates each particle from the next for detection of the parameter. In addition the increased velocity of the particles can be used to increase the throughput of the system as the detection or measurement of the parameter can be carried out more quickly.

In one arrangement the measurement of the parameters is carried out while the particles are in the duct. This has the advantage that the location of the particles is more clear and defined since it is controlled by the rotation of the body and the position of the duct. In view of the more accurate location of the particle, the measurement of the parameter can in many cases be carried out more effectively.

In this case preferably the measurement of the parameter is carried out by a measurement device carried on the rotary body. In this way the measurement device is located at a specific position relative to the duct and relative therefore to the particles. This can simplify the operation of the measurement device since it can be focused more accurately on a specific location. In this case each duct may include one or more separate measurement devices dedicated to the measurement of the particles flowing through that duct. That is each particle when moving along a duct can pass a number of sensors or measurement devices, which may be aligned in a row, where each detects a different parameter of the particle to enable a better assessment of the particle to be made. However in some cases a single sensor can provide all of the required information.

In one example each separating device comprises a separating head having a front edge arranged such that the particles to be separated move toward the front edge in a stream and an actuator for moving the front edge between a first position on one side of the stream arranged to direct the particle to a second side of the stream, and a second position on a second side of the stream, arranged to direct the particle to said one side of the stream.

In this example preferably the separating head is arranged in a radial plane of the rotating body and the first and second sides are arranged on respective sides of the radial plane.

In this example preferably the separating head includes inclined guide surfaces on the first and second sides of the front edge so that the separating head is generally wedge shaped.

Preferably the actuator is moved by piezo electric members. However other drive forces can be used for example an electromagnetic voice coil.

Berry fruits such as Saskatoons and blueberries have a short shelf life due to spoilage and need to be processed promptly following harvest. Spoiled and unripened berries are sorted out. The present invention provides a means to sort berries faster, which reduces spoilage and presents the consumer with a higher quality product.

In agriculture, crop yield is optimized by planting a specified number of seeds per unit area. Not all seeds produce viable plants. Extra seeds are planted to compensate for seeds that fail to germinate or fail to produce vigorous plants. The present invention can be used, typically on the seeding or planting apparatus, to sort seeds according to measured parameters related to viability so that seeds most likely to produce viable plants are planted and less viable seeds are used for other purposes. The present invention can be used to sort seeds according to size for compatibility with planting devices. The invention can be used to count seeds so that a specified number can be planted. The present invention can also be used provide a rapid stream of singulated seeds of known quality and number in a planting device. Because the number of singulated seeds per second provided by the present invention is much higher than prior art, a farmer can seed more acres per hour.

The invention can be applied to sorting colloidal particles, which are typically fabricated in a condensation process producing a distribution of sizes and shapes. The allowed electronic transitions in a metallic colloid depend sensitively on the size and shape of the colloid. The invention could be used to sort colloidal particles on the basis of size and shape or on the basis of absorption spectrum into homogeneous classes.

While the duct as described in some examples herein is typically a channel with upstanding sides formed in a disk, the duct can also be circular, oval, triangular or quadrilateral etc. or can be a partial tube that is generally C-shaped, V-shaped or L-shaped). The duct can also be defined by a minimal two or three dimensional surface, or surfaces defined by the points of contact imparting force on the particles. The duct can also be an enclosed tube of many different cross-sectional shapes such as circular, oval, triangular or quadrilateral.

The arrangement as described hereinafter may provide the objects to increase the kernel rate, reduce the size of equipment, and reduce the energy requirement.

The system herein can be used with conventional single operator controlled large combines or can be applied to systems using a group or an array of smaller vehicles where all of the data can be communicated from each vehicle to a central system to monitor the operation of the group. In this way the harvesting action can be monitored and controlled to cause each vehicle to separate harvested elements on a basis determined from knowledge of all of the vehicles and the selection criteria can be modified based on knowledge of the crops being harvested by all.

It will be appreciated that the harvesting machine may be stationary relative to the earth and the substrate is translated on a conveyor belt or other transfer device. The growth medium can be located on the conveyor belt or in a pot, sheet or mat or other receptacle moved along the seeding system relative to the harvesting system. In another embodiment, the substrate is carried on a conveyor belt and the harvester is translated relative to the conveyor belt in a direction that is non collinear with the direction of conveyor belt motion. Preferably the harvester is translated in a direction perpendicular to the direction of conveyor belt motion.

According to a further aspect of the present invention there is provided a method for growing crops in a growth medium comprising:

harvesting the crops and separating the collected elements of the crops from other crop material;

during the harvesting, measuring at least one property based on the collected elements and a location from which the collected elements are harvested;

and subsequently, seeding the growth medium with crop seeds using said at least one measured property.

According to a further aspect of the present invention there is provided a method for growing crops in a growth medium comprising:

seeding the growth medium with seeds for the crops;

wherein selected ones of the seeds are placed at known locations within an area of the growth medium interspersed between other seeds;

when the crops are grown on the growth medium, harvesting the crops with a harvesting machine which traverses the growth medium to collect all crops on the growth medium;

during the harvesting, harvesting the crops at the locations grown from the selected seeds separately from other crops in the growth medium, separating the harvested seeds of those crops from the other harvested crop seeds;

and collecting the separated seeds.

In an important embodiment, the harvest sort system receives seeds of different size, shape and type, separates the seeds into single file in the singulation means, measures properties of each seed, from the measured properties determines the type of seed, and separates at least one type from other types with a diverter. This important feature may be used, for example to separate seeds from two or more types of crop from one another. This important feature may be used to separate crop seeds from weed seeds. The crop seeds may for example be directed to a set of crop bins and the weed seeds may be diverted to a weed seed bin.

In some embodiments, the harvest sort system crop element measurement system is configured to measure chemical contamination from for example pesticide, herbicide or fungicide residues. The singulation system shown in FIGS. 2 and 3 is suitable for this type of measurement as inertial forces act to provide high pressure (and good contact) between crop elements and the singulation duct wall required to collect high quality attenuated total internal reflectance spectra. A portion of the duct wall may be comprised of a high refractive index material such as Si or Ge to limit the depth of radiation penetration to a micron or less. Chemical contaminants on the surface layer can be identified by characteristic absorptions in the mid infrared region, typically at wavelengths between 2.5 and 25 microns.

According to another aspect of the invention there is provided a method for growth crops in a growth medium comprising:

seeding the growth medium with seeds for the crops;

when the crops are grown on the growth medium, harvesting the crops;

during the seeding, obtaining information concerning individual seeds being seeded;

during the harvesting obtaining information concerning individual seeds being harvested;

and correlating information from the individual seeded seeds and from the harvested seeds in respect of a particular location on the growth medium.

BRIEF DESCRIPTION OF THE DRAWINGS

One embodiment of the invention will now be described in conjunction with the accompanying drawings in which:

FIGS. 18A to 18E show a series of steps in applying seeds and fertilizer to the growth medium using an application plunger which enters the ground and leaves the seed and fertilizer with a portion of the application device which remains in the ground.

DETAILED DESCRIPTION

Figure 1:
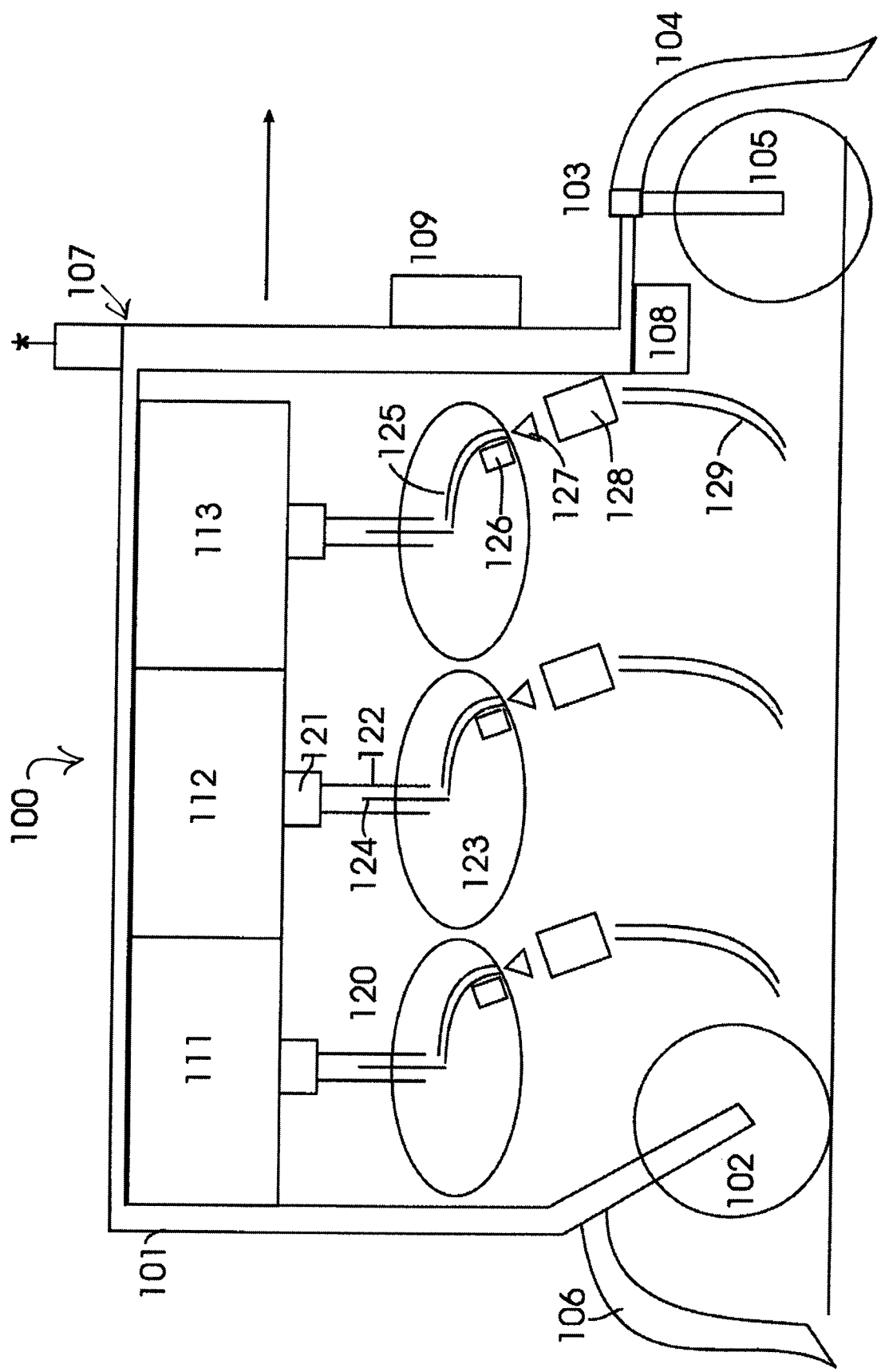
FIG. 1 is a schematic illustration of a seeding apparatus according to the present invention.

In FIG. 1 is shown a seeding apparatus 100 which includes a frame 101 on wheels 102 for transport across ground to be seeded. The frame carries one or more tool bars 103 with attached tools for preparing the soil 104, opening the soil 105 and soil closing 106. The soil opener may be a coulter for example. The specific construction of the ground engaging components is not part of the present invention and different arrangements known in the art can be used. The apparatus has a location detection device 107 and a soil sensor 108 in communication with a control device 109. The location detection device may for example be a radio receiver that operates by comparing signals from multiple beacons at known location. The beacons may be GPS satellites. Better accuracy can be achieved if the beacons are located at reference points around the field being seeded. The location detection device may also operate by laser interferometry. The soil sensor measures one or more soil parameters which may include depth, texture, moisture, organic material, nitrogen, phosphorous, potassium, and trace elements. Alternately, the soil sensor may measure infrared reflectance from the soil to infer composition. The soil sensor may detect gamma rays from isotopes in the soil to infer elemental abundances. The soil sensor may measure x-ray fluorescence to infer elemental abundances. The soil sensor may measure laser induced breakdown spectra to infer elemental abundances. The soil sensor may measure Raman spectra to infer mineral abundances. The control device 109 may combine three-dimensional location information from a series of measurements or from a previously measured topological map to predict wind, temperature and moisture conditions over a growing season at each location. The control device may further combine the wind, temperature and moisture prediction with measured soil parameters and based at least in part on at least one of the aforementioned factors select seeding parameters for that location. The seeding parameters may include the types of seed applied, the spatial relationship between seeds, and the types and quantities of other substances such as fertilizer placed proximate to each seed.

The apparatus has a plurality of compartments or containers 111, 112 and 113 for containing a plurality of separate seed types and one or more fertilizer materials to be applied to the ground. Thus in the present invention the seeding apparatus includes the storage containers 111 and 112 for seeds and optionally the storage 113 for fertilizer. In some cases only one type of seed is applied. In some cases fertilizing is carried out as a separate operation. In these cases the apparatus may include only a single compartment. The selected material from each compartment is transferred to singulator 120 for separating bulk seed or fertilizer into a stream of individual particles through supply duct 122 by bulk supply regulator 121. The bulk supply regulator may be a valve that controls the aperture of the supply duct. The bulk supply regulator may include sensors (not shown) to measure bulk parameters such as mass flow or volume flow. The bulk supply regulator may include a means to agitate bulk material to facilitate bulk flow. The system can also use a shared singulation system with a valve on each supply to control the bulk rate of each material transferred to the singulator.

The singulation device is shown and described in more detail hereinafter but includes generally a duct 125 along which the seeds pass and a disk 123 forming an assembly for rotating the duct about an axis 124 such that centrifugal forces generated by the rotation act to drive the seed radially outwardly along the duct and to cause pressure on the seed against one side wall of the duct to slide along the wall. Only one duct is shown, but there may be a plurality of singulation ducts 125. As the singulated particle rate from a single duct of the present invention can be more than ten times higher than prior art singulators, a single duct is usually sufficient for seeding applications. The rate limiting factor for the present invention is the power required to operate ground opening and ground closing tools rather than the singulation rate.

Figure 6:
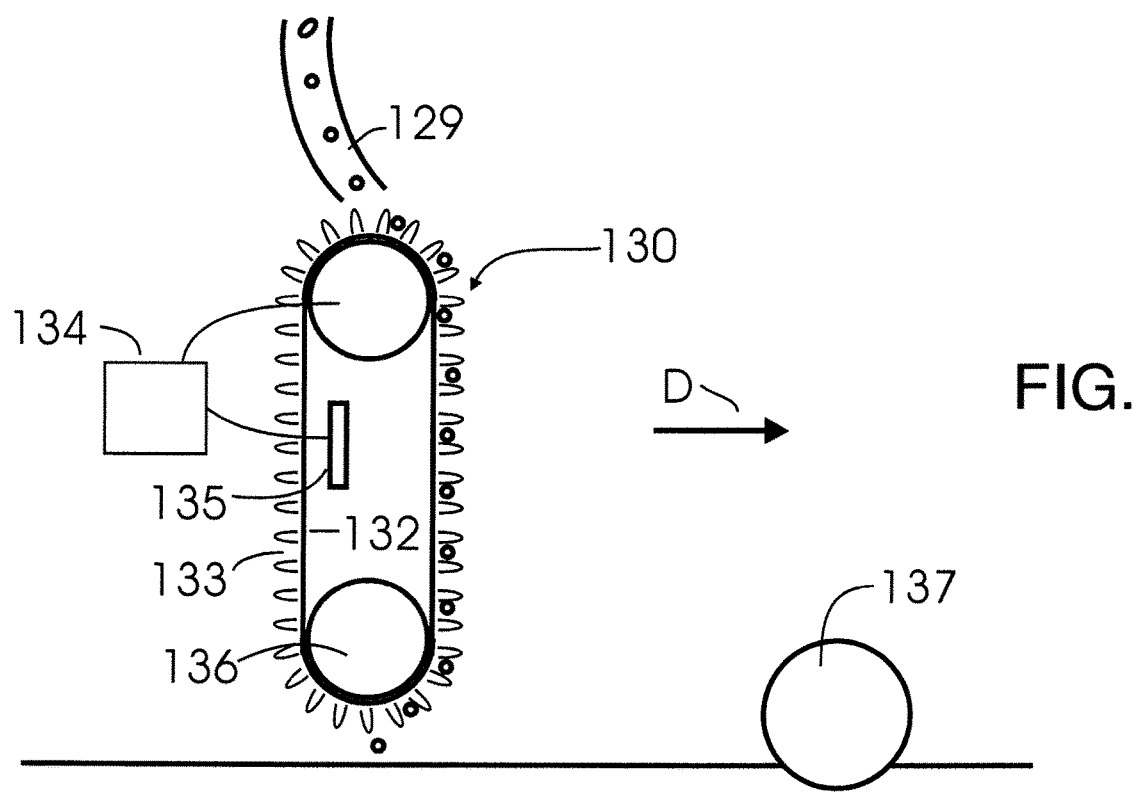
FIG. 6 is a schematic illustration of a second embodiment of the singulation and transfer devices of FIG. 1.
Figure 7:
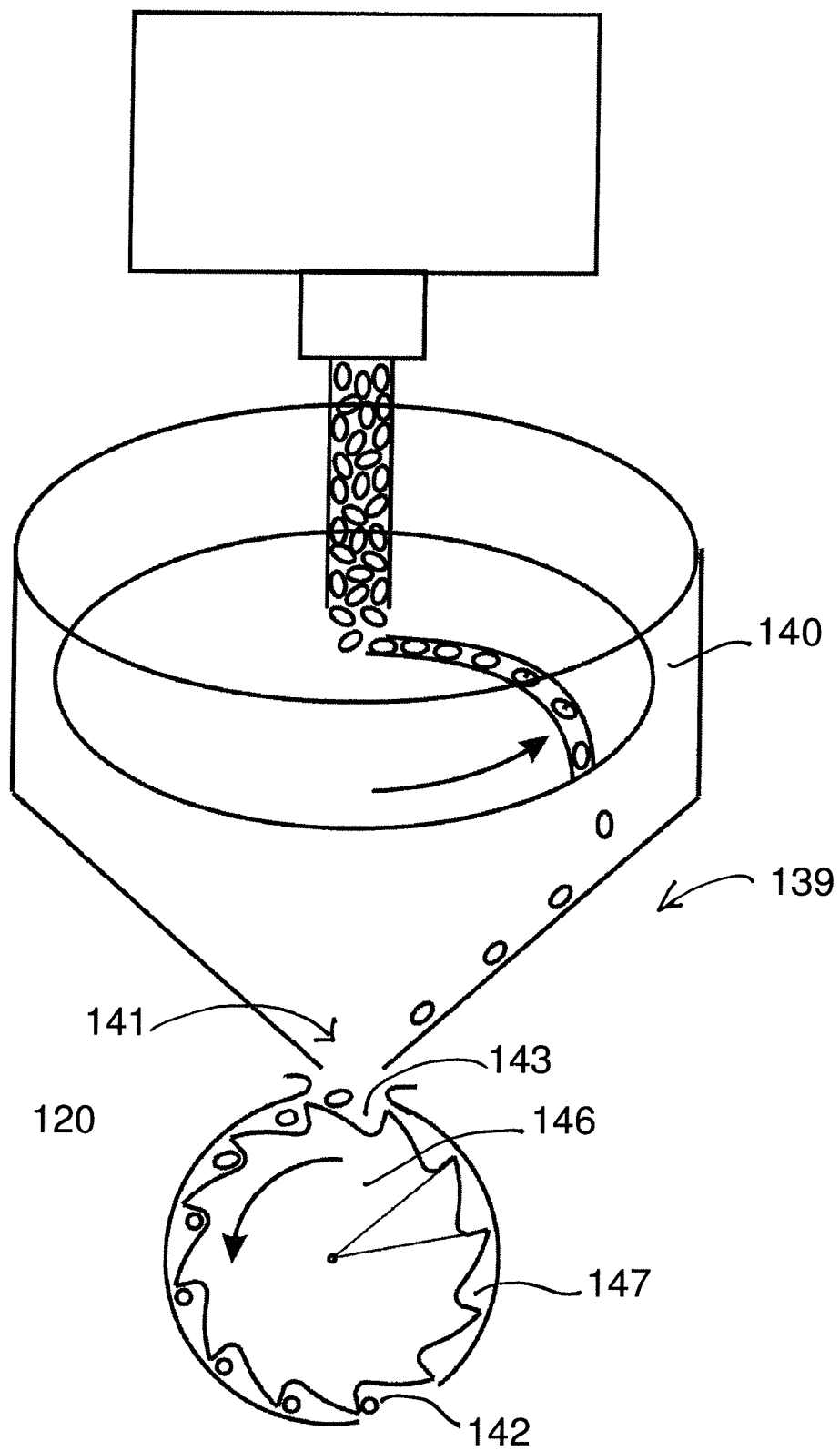
FIG. 7 is a schematic illustration of a further embodiment of the singulation and transfer devices of FIG. 1.

This forms a stream of the seeds or fertilizer pellets (collectively particles) at singulated or separated locations along the duct so that they emerge from the end of the duct one after for planting. The stream of particles emerges from the end of the singulator duct 125 at a radius R from the axis of rotation and with a velocity vector dependent on the angular displacement of the singulation duct 125. A conditioning device 128 such as shown in FIGS. 6 and 7 operates on the position dependent stream of particles to direct the stream of particles toward one or more exit ports. The stream of particles at the exit port of the conditioning device is directed into a delivery device 129. The delivery device operates to deposit the stream of particles on the soil or substrate. In the simplest embodiment, the delivery device can be a seed tube of conventional design.

The conditioning device may also operate to reduce the variance in the period between consecutive particles. Specifically, the average period T and the variance of the period are related to the size and shape of the particles as well as the shape, friction and rotational velocity of the singulation duct. For example, an ellipsoidal seed like a wheat kernel will initially line up in the singulator with the long axis generally aligned with the duct axis with some variation in the center of mass spacing due to differences in kernel size and inter-kernel contacts along lines that don't correspond with the long axes of the kernels. The separation between kernels increases in proportion to the initial inter-kernel distance as the kernels are accelerated by inertial forces due to rotation of the duct 125. Hence a 10% variation in inter-kernel distances in the bulk will lead to a 10% variation in the period between kernels at the end of the singulator duct 125. The variation in period directly leads to variation in seed placement by the same factor. The conditioning device may operate to reduce the variation in period from for example 10% to 1% by temporarily buffering the particles before release as described in further detail hereinafter with reference to FIGS. 6 and 7.

As shown hereinafter, the disk 123 includes a measurement device 126 for detecting one or more parameters of the seeds and a diverting device 127 for extracting some of the seeds so that only selected ones of the seeds are applied in the seeding action. A control system 109 acts to receive data from the measuring devices and from a location system 107. The control system acts for recording measurements of the seeds relative to time and/or recording measurements of the seeds relative to location on the ground.

The control system can also act for providing information about the ground, either by a previously prepared map related to the location system 107, or by a ground sensor 108 which acts to obtain in real time data about the condition of the ground. This data is used to determine for the actual location of the ground into which the seeds are to be applied to transfer seeds selected types or numbers of seeds to be applied depending on the information.

When the seeder is used to select certain seeds from the supply to reduce the number or to seed selected seeds from the containers 111, 112, the diverting device is operated for diverting selected seeds away from the ground opening device in response to the detecting of at least one parameter of the singulated seeds and to transfer those seeds either back into the singulated stream or back to a storage container which can be the original container.

In particular the system can be operated so that the singulation rate is higher than a minimum required rate of seeds to be applied to the ground so that a replacement seed is available, from the stream or from the stream of the other container or containers, in instances where a first tested seed does not meet a condition to continue to the transfer device and is discarded.

In particular, the first and second separate containers 111, 112 can contain respective seeds with first and second quality parameters and the control device 109 selects which container is used based at least in part on at least one measured parameter of the seeds and/or the ground. Further, detector 126 may measure seed properties and control 109 determines whether measured seed properties match required seed properties for the present seeder location within thresholds. If the properties match, the seed continues to delivery device 129, otherwise the seed is diverted. This feature can be used for example to detect and reject seeds that have deteriorated during storage.

The container 113 and its respective singulation device provides a system for supplying fertilizer pellets and/or powder and/or liquid fertilizer where the volume or the number of fertilizer pellets placed per unit length can be varied to bring the concentration of fertilizer at each location to a desired level.

Figure 2:
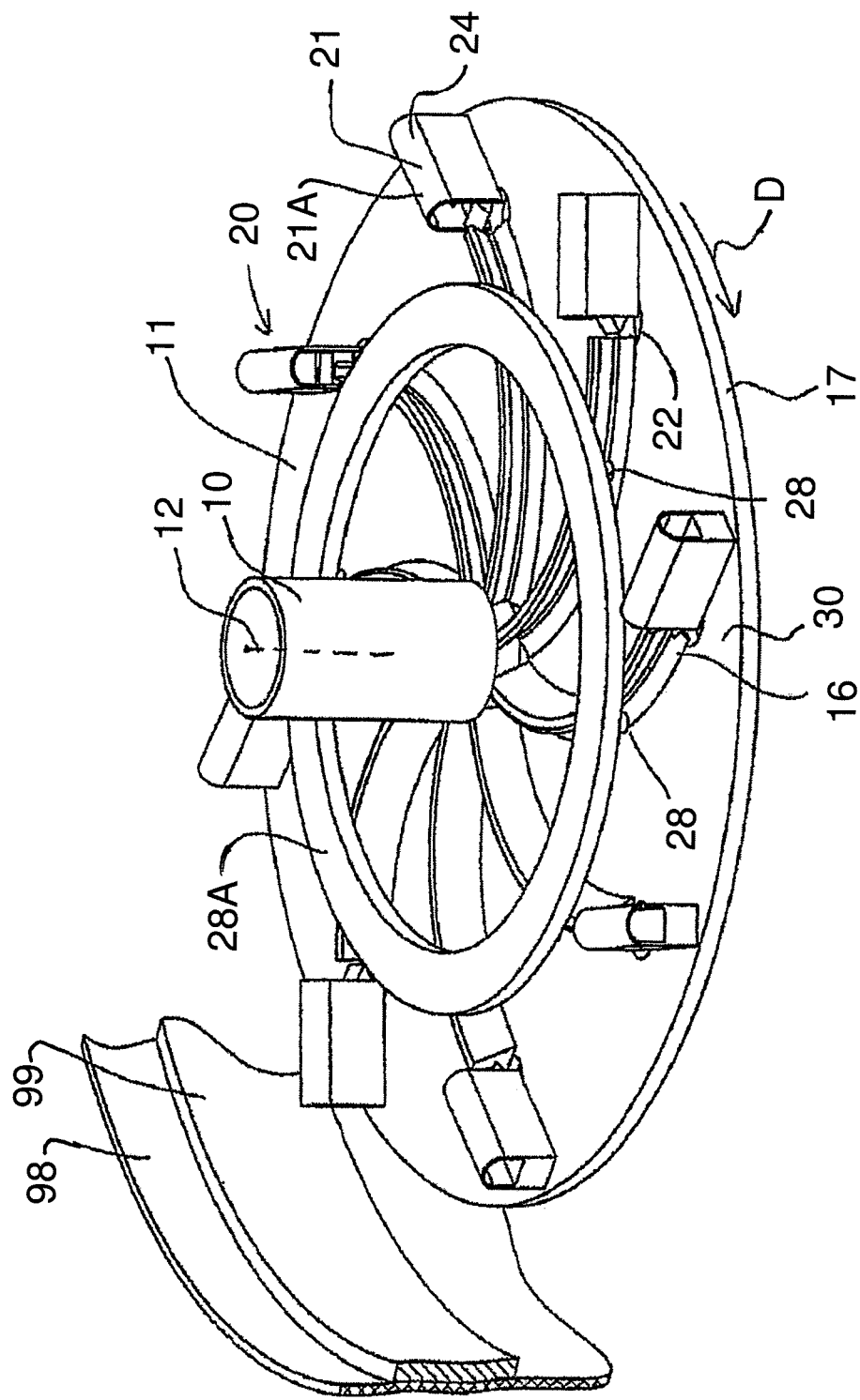
FIG. 2 is an isometric view of a seed sorting apparatus showing a method of particle singulation according to the present invention.
Figure 3:
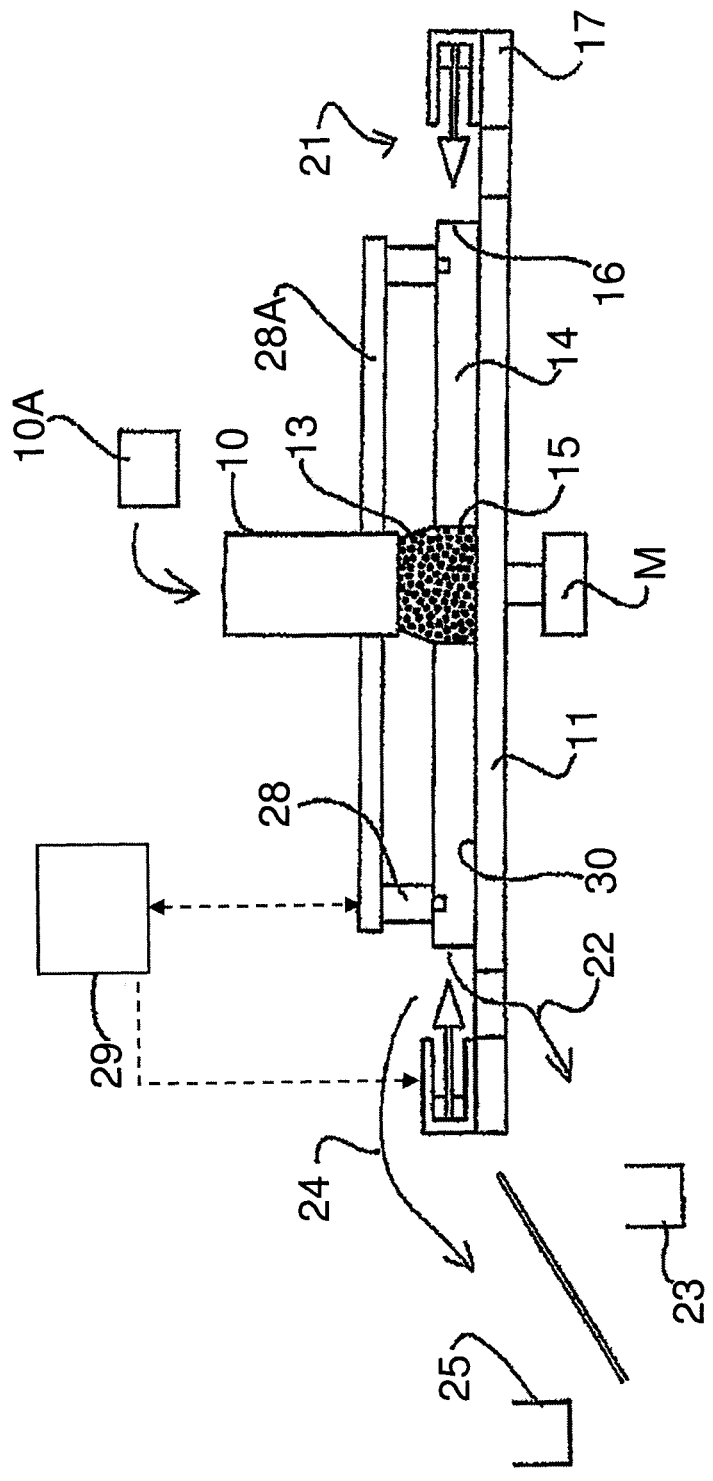
FIG. 3 is a vertical cross-sectional view through the apparatus of FIG. 2.

The apparatus for sorting particles based on a measurable parameter of the particles shown in FIGS. 2 and 3 comprises a supply conduit 10 carrying particles to be sorted from a feed supply 10A (FIG. 3) which supplies the particles in a continuous stream for presentation through the conduit to a rotary body 11 rotatable around an axis 12. In the embodiment shown the rotary body is a flat disk with the axis 12 arranged vertical so that the disk provides an upper horizontal surface onto which the particles 13 are supplied in the stream from the conduit 10. The conduit is arranged at the centre of the disk so that the particles are deposited onto the centre of the position where the disk is rotating but where there is little outward velocity. The kernel velocity at this point is from the flow in the supply conduit 10. The velocity at a point on the disk is v=wr where w is the angular velocity and r is the radius. If kernels are deposited in a region where the change in velocity is too high, they bounce and the flow is chaotic. Kernels are deposited in the central region to minimize the change in velocity.

On the upper surface of the disk forming the rotary body is provided one or more ducts 14 (FIG. 3) each extending from an inner end 15 adjacent the axis outwardly to an outer end 16 spaced at a greater radial distance outwardly from the axis than the inner end. In this embodiment the outer end 16 of the ducts is arranged adjacent to but spaced inwardly from the edge 17 of the disk 11. In this embodiment each duct 14 extends from a position closely adjacent the centre to the periphery 17 of the disk so that the centre the ducts are arranged immediately side by side and the ducts diverge outwardly so that at the outer end 16 they are spaced around the periphery 17.

The inner ends 15 are thus arranged in an array adjacent to the axis so that the supply conduit 10 acts to deposit the particles to be sorted at the inner ends 15 of the ducts for entry of the particles to be sorted into the inner ends. As the inner ends are immediately adjacent at the centre of the disk, the particles there form a pile at the centre which is automatically sorted evenly in to the open mouths of the ducts at their inner ends. Assuming a continuous pile of the particles at the centre, the rotation of the disk will act to evenly sort the particles into the individual ducts in a stream defined by the dimensions of the mouth relative to the dimensions of the particles. At the outset of the path along the duct, the particles will be immediately adjacent or overlapping. However passage of the particles along the duct while they are accelerated by the centrifugal forces will act to spread the particles each from the next to form a line of particles with no overlap. As the forces increase with increasing radial distance from the axis 12, the particles will be increasingly accelerated and thus the distance between particles will increase along the length of the duct. The kernels align with the duct axially in the first part of the duct and the kernel length defines an initial center to center spacing with some variation due to differences in kernel size. The centrifugal acceleration is uniform at a given radius, but the frictional forces for grain kernels vary by about 20%. The frictional forces scale with the Coriolis force $F_{friction}=uN$, where u is the coefficient of friction (approximately 0.2-0.25 for wheat kernels), and N is the normal force to duct wall supplied primarily by the Coriolis force. As set out above, the duct can be shaped to minimize the normal force and friction by curving the duct along the line of net force as mentioned in text earlier. Conversely, the particle acceleration can be reduced by curving the duct to increase normal forces, curving the duct to constant or even decreasing radius, or increasing the coefficient of friction of a selected portion of a duct by changing the texture and/or material.

Selection of the length of the duct relative to the size of the particles can be made so that the spacing between each particle and the particle behind can be selected to be a proportion of the length of the particles. The separation between seeds can be increased by increasing the rotation rate, the radial extent of the duct, or both. In the example where the separator is used for seeds, the separation between each seed and the next can be at least equal to the length of the seeds and typically 1.5 or 2.0 times the length of the seed. This separation is sufficient for operations such as measurement and diversion to be performed on individual seeds. Larger separations are possible, but reduce the duty cycle of measurement and increase impact forces in diversion and are thus less preferred.

Thus the ducts are shaped and arranged so that the particles are accelerated as they pass from the inner end to the outer end so as to cause the particles to be aligned one after the other in a row as they move toward the outer end.

The outer ends 16 are arranged in an angularly spaced array at an outer periphery of the rotary body so that the particles of the row of particles in each duct are released by centrifugal force from the disk outwardly from the axis of the disk. The openings all lie in a common radial plane of the disk. The ducts can be formed either as grooves cut into the upper surface of a thicker disk or by additional walls applied on to the top surface of the disk, or two-dimensional and/or three-dimensional shaped guides.

An array 20 of particle separating devices 21 is arranged in an annulus at the outer edge 17 of the disk so that the individual separating devices 21 are arranged at angularly spaced positions around the disk.

Figure 4A:
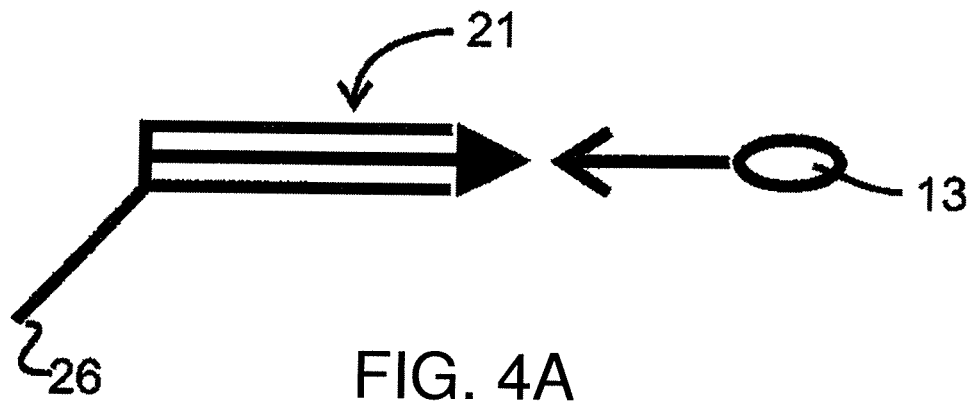
FIGS. 4A, 4B and 4C show vertical cross-sectional views through the separating device of the apparatus of FIGS. 2 and 3.
Figure 4B:
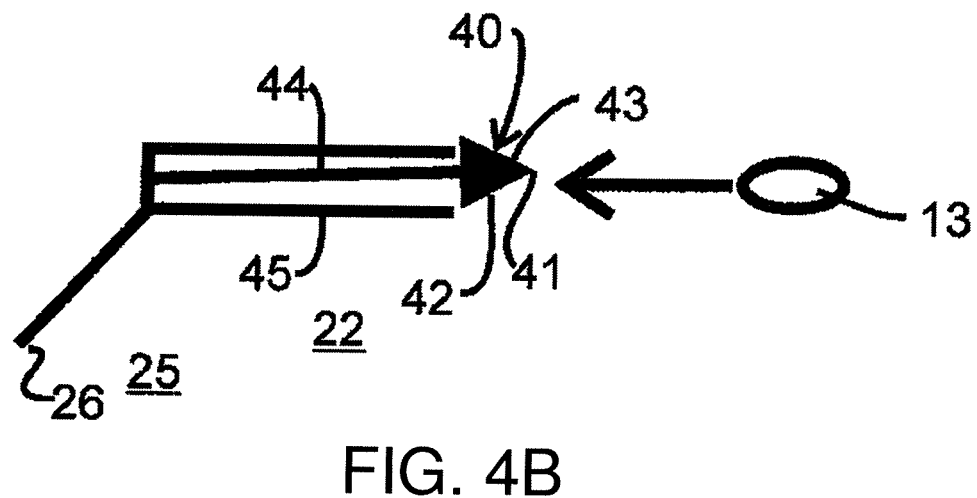
Figure 4C:
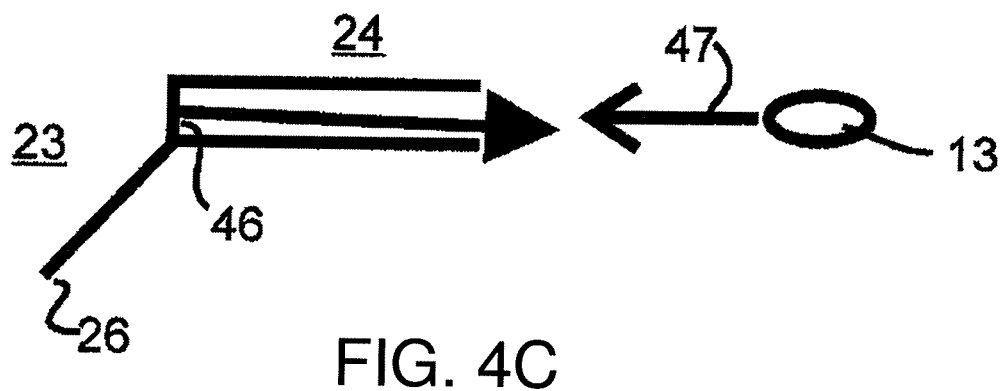

Each separating device is operable to direct each particle into one of a plurality of paths as determined by operation of the separating devices. In the example shown the separating devices are arranged to direct the particles upwardly or downwardly relative to the plane of the outlets 16. As shown in FIG. 2 and FIG. 4A the separating device 21 can take up an initial intermediate or starting position where the particles are not separated to one direction or the other. As shown in FIG. 4B, the separating device can be moved upwardly so as to direct the particles downwardly into a path 22 for collection within a collecting chamber 25. Similarly when the separating device is moved to a lowered position as shown in FIG. 4C, the particles are moved upwardly over the top of the separating device along a path 24 for collection within a chamber 23. The two paths 22 and 24 are separated by a guide plate 26 which ensures that the particles move to one or other of the chambers 23, 25.

In order to control the separating devices 21, there is provided a measuring system generally indicated at 28 which is used to measure a selected parameter or parameters of the particles as those particles move from the end of the duct at the edge of the disk toward the separating devices. The measuring devices are carried on a mounting ring 28A.

The measuring system can be of any suitable type known in this industry for example optical measuring systems which detect certain optical characteristics of the particles to determine the particular parameters required to be measured. Other measuring systems can also be used since the type of system to be used and the parameters to be selected are not part of the present invention.

In a typical example, the analysis of the particles relates to the presence of degradation of the seed due to disease and this can often be detected optically for example using the systems and disclosed in the prior U.S. Pat. No. 8,227,719 of the present inventor, the disclosure of which is incorporated herein by reference or may be referenced for further detail.

Each separating device 21 is associated with a respective detecting device 28, which may include multiple detecting components, operable to measure the parameter of the particles and in response to the parameters measured by the associated detecting device, the respective or separating device is operated to select the path 22 or the path 24.

It will be appreciated that the number of paths can be modified to include more than two paths if required depending upon the parameters to be measured. Such selection to an increased number of paths can be carried out by providing subsequent separating devices 21 positioned downstream of the initial separation. In this way one or both of the paths can be divided into two or more subsidiary paths with all of the separating devices being controlled by a control system 29 receiving the data from the measuring device is 28.

The disk 11 thus has a front face 30 facing the supply conduit and the ducts 14 lie in a radial plane of the disk and extend outwardly from the axis to a periphery 17 of the disk 11.

As shown in FIG. 2, the ducts 14 are curved so that the outer end 16 is angularly retarded relative to the inner end 15. This forms a side surface 14B of each duct which is angularly retarded relative to the direction of rotation in the counter clockwise direction as shown at D. This curvature of the ducts is arranged to follow substantially the Coriolis and centrifugal forces so that the particles follow along the duct without excessive pressure against either side wall of the duct. However the shape of the duct is arranged so that the Coriolis forces tend to drive the particle against the downstream side 14B of the duct 14.

As shown best in FIG. 2, the ducts 14 are immediately side by side at the inner ends 15 adjacent the axis and increase in spacing toward the outer ends 16. At the inner ends 15 the ducts are immediately side by side so that the maximum number of ducts is provided by the maximum number of openings 15. The number of ducts can be increased, in an arrangement not shown, where the ducts include branches so that each duct divides along its length into one or more branches.

In the embodiment of FIGS. 2 and 3, the detection device 28 and the separating device 21 are both located within the periphery 17 of the disk. In this way the particles are guided as they pass from the outer end of the ducts to the array of separating devices.

As best shown in the FIGS. 4A, 4B and 4C, each separating device comprises a separating head 40 having a front edge 41 lying generally in a radial plane of the disk 11 so that particles released from the outer ends 16 move toward the front edge 41. The separating head 40 includes the inclined guide surfaces 42 and 43 on respective sides of the front edge 41. In this way the separating head 40 is generally wedge shaped. The separating head is mounted on a lever 44 mounted inside a tube 45 so that the lever and the actuating mechanism for the lever are protected inside the tube which is located behind and protected by the separator head. An actuator 46 is provided for moving the front edge 41 between first and second positions above and below the radial plane 47 defined by the path of the particle 13. Thus in FIG. 4A a central and neutral position is shown. In FIG. 4B the front edge 41 has moved upwardly which is arranged to direct the particle to a side of the radial plane below the radial plane. In the position shown in FIG. 4C, the front edge is moved downwardly to a second side of the radial plane and is arranged to direct the particle to the first or upper side of the radial plane. This movement of the wedge shaped head and its front edge requires little movement of the front edge 41 and uses the momentum of the particle itself to cause the separation simply by the particle sliding over the guide surfaces 42 and 43. The separation head therefore does not need to move into impact with the particle or to generate transverse forces on the particle since the head merely needs to move into position allowing the particle to generate the required separation forces.

In view of the provision of the lever, the actuator 46 required to generate only small distance movements and hence can be moved by piezo electric members. Alternatively the movements can be carried out by a small electromagnetic coil. This design allows the use of components which can generate the necessary high-speed action to take up the two positions of FIGS. 4B and 4C sufficiently quickly to accommodate high-speed movement of the particles. As shown the actuator 46 is located outward of the separating head and lies in a radial plane of the separating head.

The arrangement of the present invention therefore provides a system for separation of the particles, for example kernels, where the particles are supplied in a feed zone and are separated by the ducts and the inlet of the ducts so as to form a plurality of streams of the particles.

Figure 8:
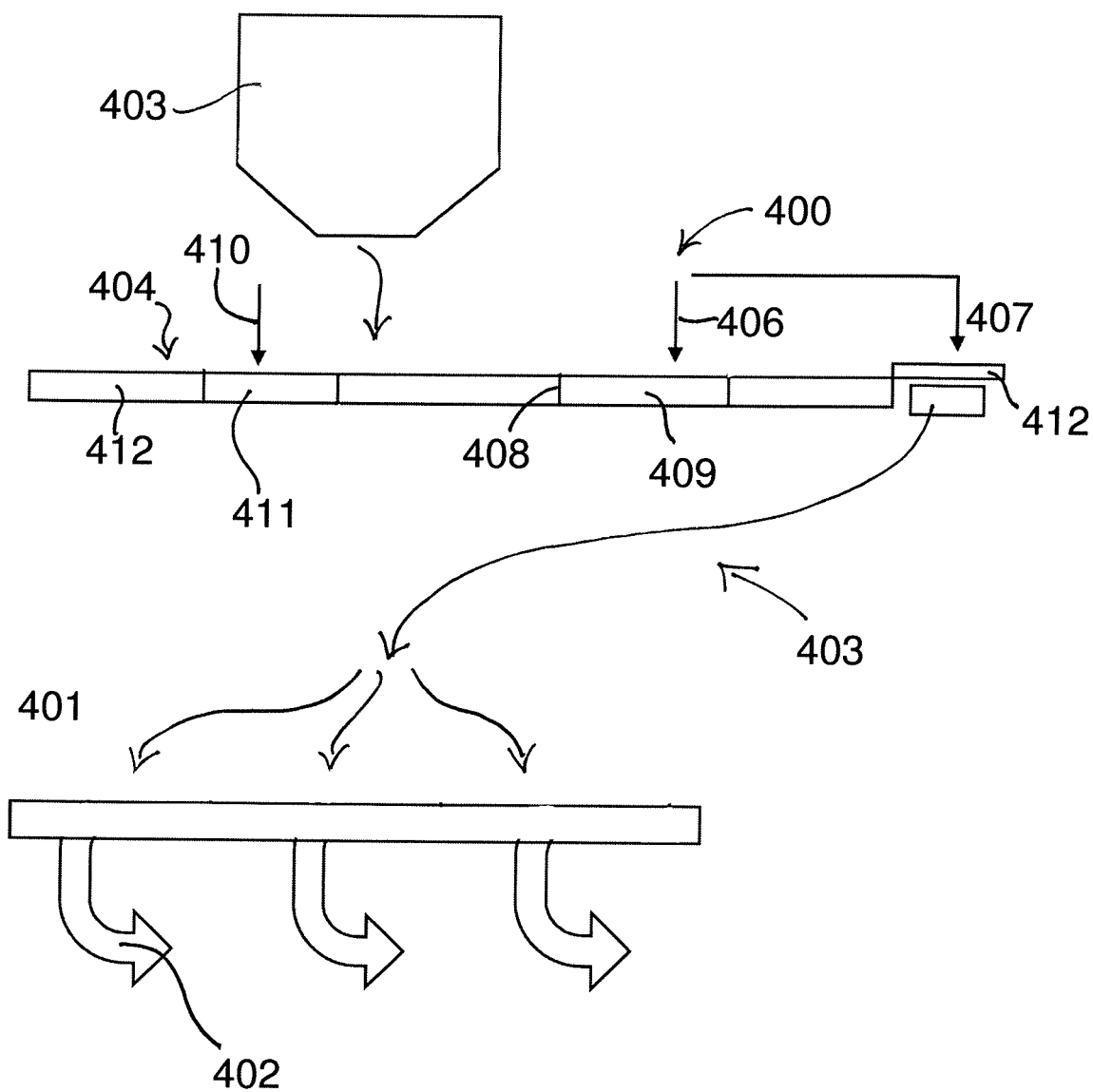
FIG. 8 is a schematic illustration of a yet further embodiment of the singulation and transfer devices of FIG. 1.

As shown in FIG. 8, there is shown a seeding system generally indicated at 400 including a seeding tool bar 401 on which is mounted a series of individual planting devices 402. Each planter 402 is fed with seeds by a transfer duct system 403 which is fed with seeds from a separator 404 generally as described above where a hopper 405 supplies seeds to the separator.

Thus the measurement and separation system of the present invention is used on the seeding or planting apparatus 400 to sort seeds according to measured parameters related to viability so that seeds most likely to produce viable plants are planted and less viable seeds are used for other purposes. The present invention can be used to sort seeds according to size as detected by a sensor 406 for compatibility with planting devices. The sensor 406 can be used to count seeds so that a specified number can be planted or packaged. The arrangement also provides a rapid stream of singulated seeds separated by the separator 407 of known quality and number in a planting device. Because the number of singulated seeds per second provided by the present invention is much higher than prior art, a farmer can seed more acres per hour.

Also as shown schematically in FIG. 8, the separation of the particles at separator 407 can be carried out using electrostatic forces where the particles are charged differentially according to selected parameters and then passed through an electric field 412 so that the differential charging causes the particles to divert to different paths.

Figure 5:
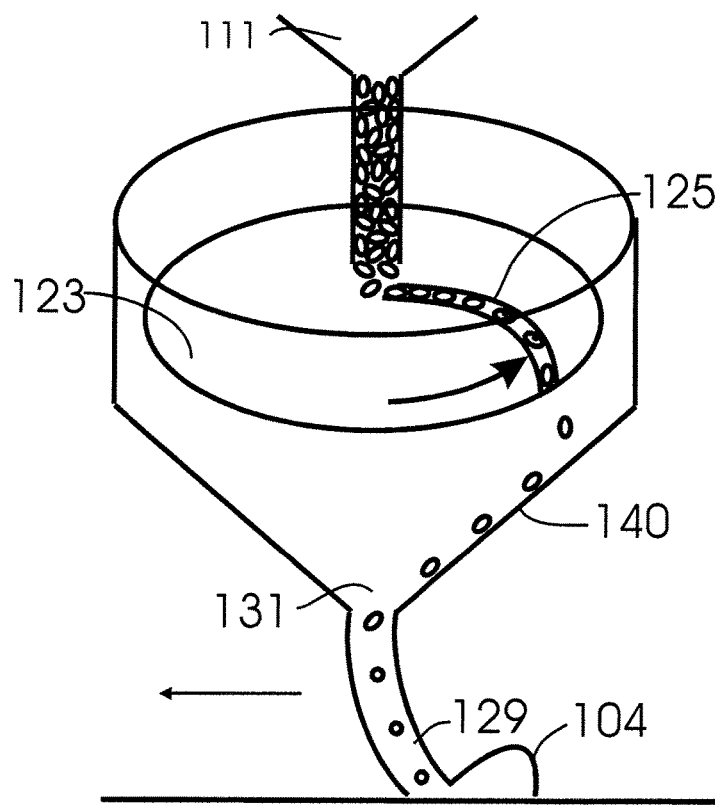
FIG. 5 is a schematic illustration of one embodiment of the singulation and transfer devices of FIG. 1.

As shown in FIG. 5 there is a simple transfer system which the singulated seeds in the stream from duct 125 on disk 123 are discharged into a container 140 surrounding the disk so that the seeds flow in the singulated stream out from a bottom opening 131 through a duct 129 to the ground engaging component 104. This system does not provide any measurement of the parameters of the seeds and acts only as a high speed singulator.

As shown in FIG. 6, the seeds from the bottom of the duct 129 are fed instead to a transfer member 130 in the form of a belt 132 with compartments 133 for containing the seeds and carrying them to the ground behind a ground opener 137 in this case defined by a coulter. The belt can be of the type known as a brush belt where bristles on the belt form an array of locations or individual receptacles for the seeds. The transfer member 130 acts for transferring the singulated seeds to or behind the ground opening device for placement in the opened ground. In this case the transfer device defined by the belt can operate at different speeds of transfer by a motor controller 134 controlled by an encoder 135.

Thus in this arrangement the singulation device acts to singulate to spacings between the seeds having different lengths due to the fact that the seeds are not accurately carried from the duct 125 and through the duct 129. This causes some uncontrolled changes in spacing.

In order to overcome this non-regular spacing, the transfer member or belt operates at timed different timed intervals to change the difference between the spacings either to reduce the difference or to intentionally place the seeds at uneven intervals on the substrate. That is the transfer device comprises a belt with receptacles for the seeds wherein the belt is driven at different forwarding speed to change intervals. The spacings between the seeds are measured by a sensing system which can be provided by the measurement device 126 or by simple optical detectors past which the seeds flow. This spacing is then communicated to the controller which controls the speed of the belt 132.

Also as shown in FIG. 6, the belt 132 wraps around a drive roller 136 so that the belt moves opposite to the direction D of forward movement of the seeder. In this way the transfer device is arranged such that the velocity of a seed exiting the transfer device is approximately equal in magnitude and opposite in direction to the relative velocity D between the ground opening device 137 and the ground.

As shown in FIG. 7 the transfer device generally shown at 139 comprises a funnel 140 feeding into a slot or gate 141 that feeds particles into a pocket 143 shaped to direct particles toward a back wall of pocket 143 by acceleration of actuator 146. The particles are constrained to remain in the pocket during transit from feeding slot 141 to exit port 142 by casement 145. Particles or seeds are discharged from exit port 142 for seeding via seed tube 150. The acceleration of actuator 146 may be rotational as shown or linear (not shown). The rotational speed of the actuator (in revolutions per second) is the particle or seed rate in Hz divided by the number of pockets. The angular range of a pocket 147 is chosen in combination with the particle rate such that singulated particles from channel 125 on disk 123 each fall into a different pocket. Particles are released from channel 125 in a sequence with a constant average period, but with random phase with respect to required particle placement timing requirements. Frictional forces broaden the probability of a particle arriving at slot 141 with time. The transfer device 139 functions to reduce the width of the particle probability function and to shift the phase for synchronization of particle placement as illustrated at 149. Seed tube 150 is arranged to translate in two orthogonal directions. The motion of the seed tube and the velocity of the actuator is coordinated by a controller (not shown) to deliver seeds at any chosen position on the ground or growth substrate (within the range of motion).

Figure 9:
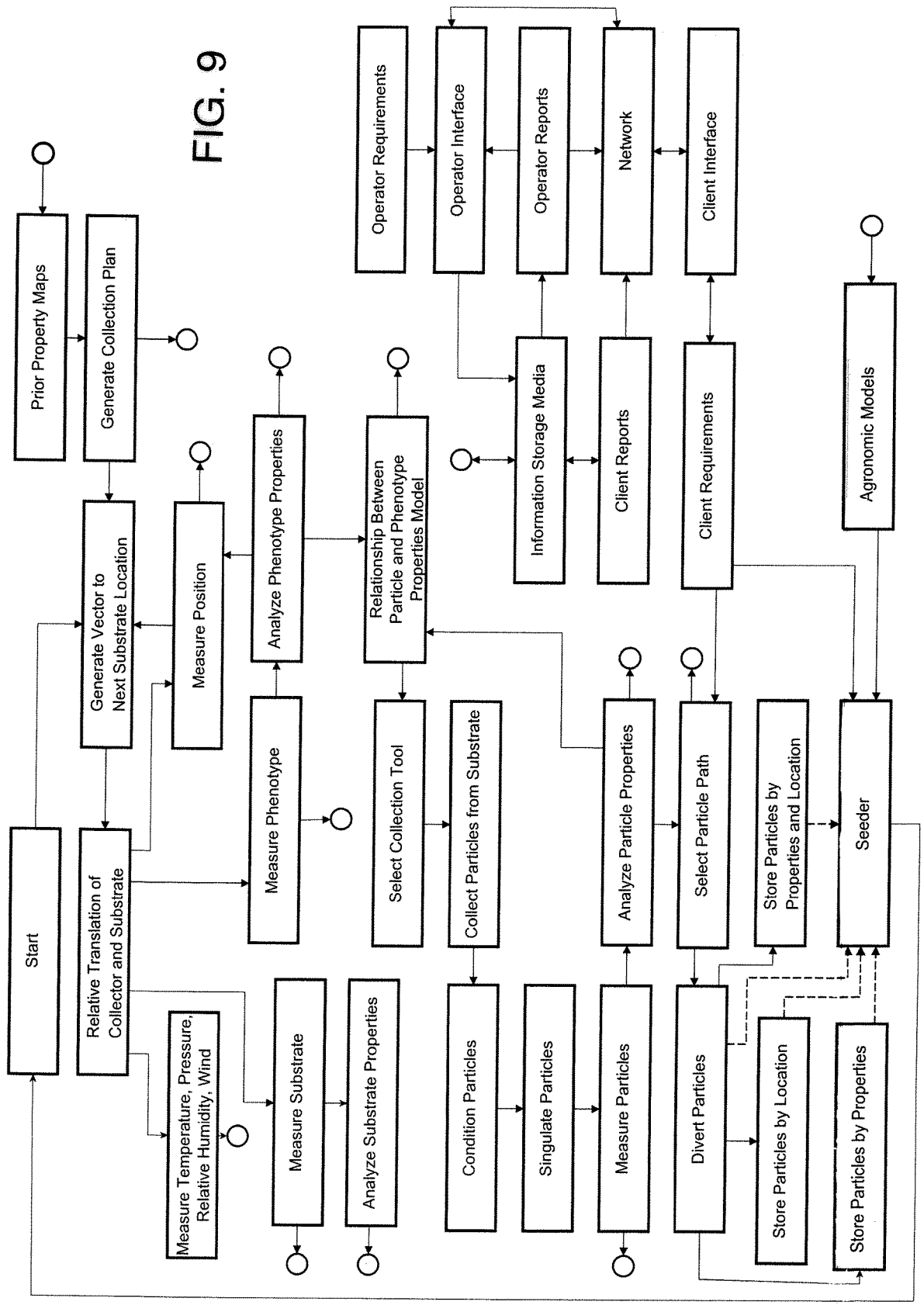
FIG. 9 is a flow chart of the harvesting system.

A flow chart for the logic at each translation step of the harvest sort system (HSS) is given in FIG. 9. For simplicity a connection to local information storage and external information exchange is denoted by a circle.

The HSS as shown takes sensor measurements of weather, substrate, crop phenotype and location at each step. The weather information may be used immediately to, for example, adjust the cutter parameters to changes in straw texture with temperature and humidity. Secondly the weather information can be correlated with crop quality parameters and used to predict optimal harvest conditions for future crops. The substrate sensor information can be compared with substrate information collected during seeding operations to assess changes in the substrate composition during the growing season. The changes in substrate composition can be used to improve the agronomic model and determine required fertilizer inputs for future crops. The phenotype sensor measures plants immediately in front of the harvester unit and the data is analyzed to provide information about each plant in the field of view. Information about the type of plant may be combined with location information from a location sensor reading external beacons such as GPS or local field beacons to infer position relative to known seed locations with high accuracy. The location sensor establishes a search region for a pattern of plant phenotypes and the pattern of plant phenotypes within the region is compared with patterns stored by a seeding operation to identify the location of the harvester relative to the stored locations of individual seeds as for example shown in the following FIGS. 10A, 10D and 10E and from the patterns identify the provenance of each plant. That is the system can use position within a pattern to look up properties of each seed placed in a prior seeding operation using the system of the present invention. The harvester may on a plant by plant basis retrieve information about the properties of the seed that produced the plant, properties of the substrate the seed was placed in, phenotypic properties of the plant, and details of the agricultural inputs used with the plant. This information may be combined with weather information from the growing season to improve the agronomic model for subsequent seeding operations. The phenotypic properties of the each plant may be correlated with properties of elements harvested from said plant. The harvested may use the correlation to select the means used for harvesting each plant. As discussed herein after (FIG. 21), the harvested may select an auxiliary harvester to harvest individual plants or a general harvester to harvest those plants not individually selected. The properties of crop elements individually harvested plants may be directly correlated with the seed that produced the plant, the plant phenotype, agricultural inputs, weather, and substrate properties. The properties of crop elements in the general harvest can be statistically linked to the properties of the plants within the general harvest region at a given time of harvest.

These features of the present invention are very useful for breeding crop types well suited to each location in a field. The harvester of the present invention harvests both crop material and information.

The harvest sort system preferably uses the singulation and sorting system shown in FIGS. 2, 3 and 4 to singulate and individually measure each harvested crop element. The harvested crop elements may be diverted to separate bins based on location in the field, properties of the harvested crop element, or both. Selected harvested crop elements may be directed directly to a seeding operation of the present invention. Alternately, stored crop elements may be directed to a seeding operation by a seeder of any type at a later date.

A client may have contracted a set of assigned locations from a prior planting operation with the present invention and the harvester places crop elements from those assigned locations in a separate bin or bins for the client. A client may specify a set of property requirements for harvested crop elements (or the harvested plants) and the harvester directs crop elements meeting the client requirements to bins assigned to the client. The harvester may provide the client with real time information about fulfillment of contracted volumes or properties via a network connection.

Figure 21:
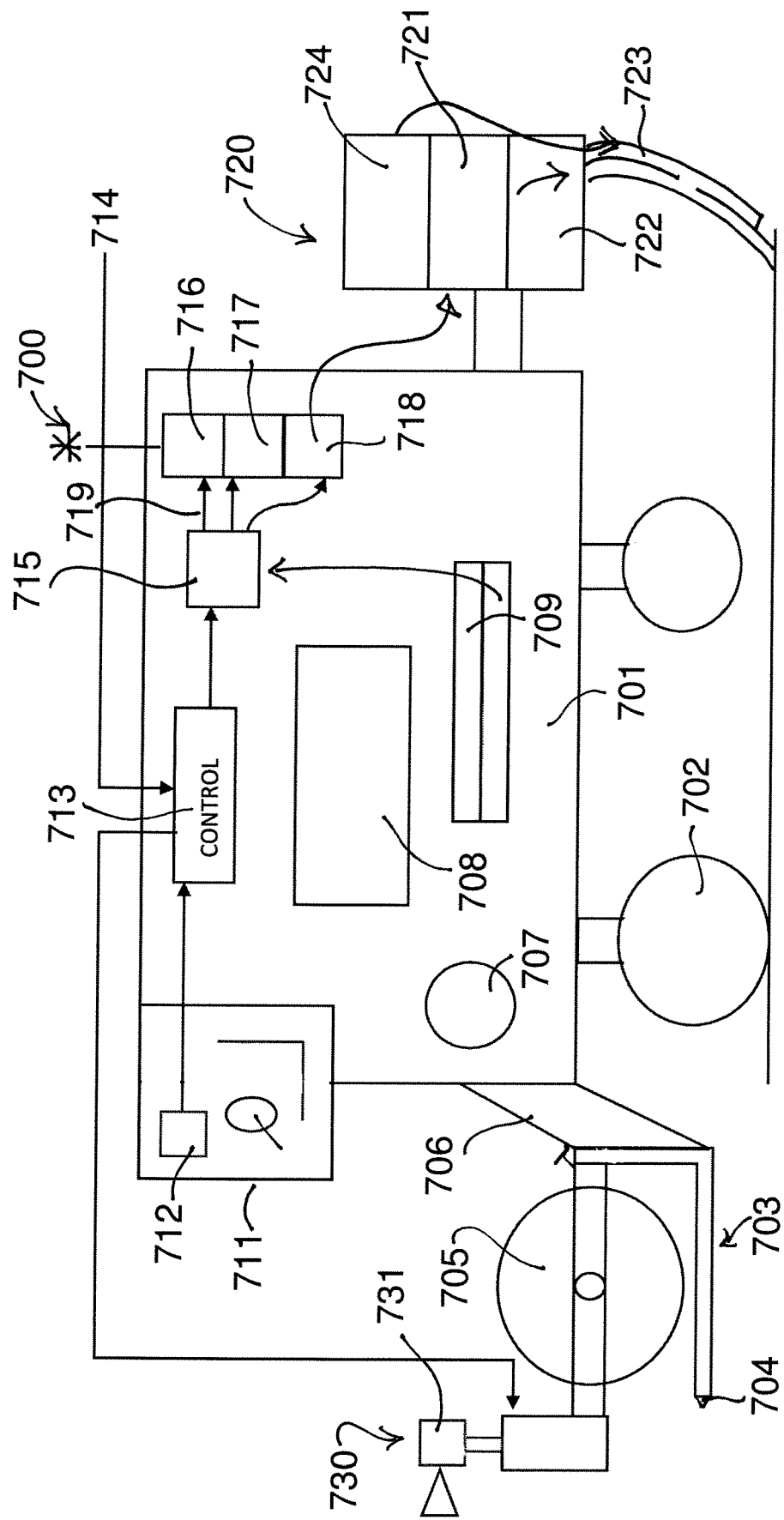
FIG. 21 is a schematic illustration of a harvester using the arrangements described herein.

The harvest sort system shown in FIGS. 9 and 21 can in principle provide the operator with real time information about each individual crop element harvested. In practice the operator receives statistics about the number, volume or mass of crop particles that fall within each operator designated property class. The operator may for example use the information to adjust class parameters to meet marketing requirements. The operator may coordinate the operation of multiple harvesting units at geographically separated locations to collect crop elements from each location that meet a property criterion.

FIGS. 10A to 10E show a method for growing crops where, during the seeding, the seeds are placed in different patterns in the growth medium where the patterns define respective different locations in the growth medium. This pattern system can be used at a later proceed by any reader to identify accurately the location on the growth medium. Thus GPS can be used to identify a general area which might be of the order of 1 meter in area and subsequent to seeding in patterns in the area so defined, the system operates for identifying the different locations by reading the different patterns.

The pattern can be one dimensional in either the transverse or longitudinal direction or more preferably is two dimensional in both the transverse and longitudinal direction to determine a specific location in the substrate.

Figure 10A:
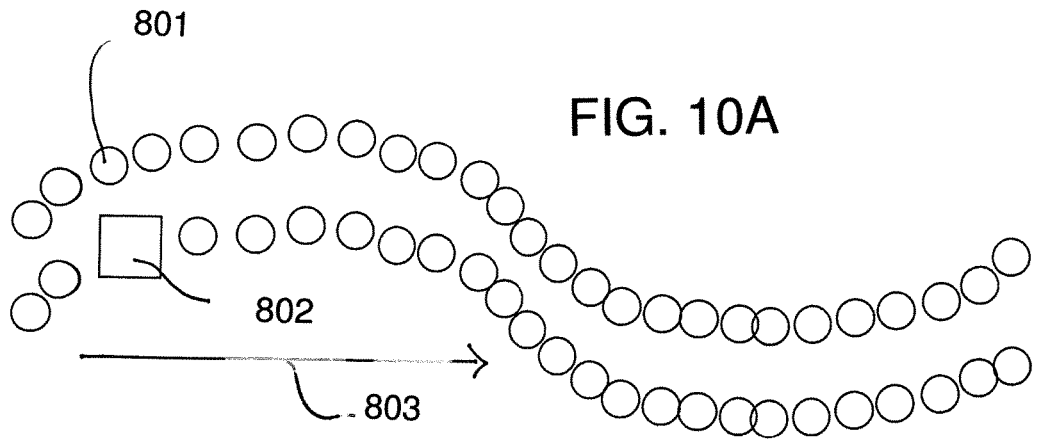
FIG. 10A illustrates a scheme for encoding position information in a pattern with two types of seeds.

FIG. 10A shows a possible position encoding pattern with two types of plants. One period of a waveform is shown. The upper curve consists only of plants of a first type 801 and the lower curve includes one plant of a second type 802. The number of plants of type 802 and their position in a waveform may be used to distinguish one curve from another transverse to the direction of the waveforms 803. A pattern of plant of type 802 may also be used to indicate the phase of a waveform. A sensor on the harvester collects data and a computation means analyses the data to generate plant generate an internal representation of plant positions and phenotypes to shown schematically in FIG. 10A. The computation means then compares the measured pattern and stored seeding patterns and finds the best match. The computation means next assigns a seed from the stored seed positions to each plant in the pattern. The computation means also identifies seeds that failed to germinate by analysing the sequence of plants for gaps. The computation means may further analyse the phenotype properties, associated seed properties and measured location properties to provide information that improves the predictive accuracy of the agronomic model.

Figure 10B:
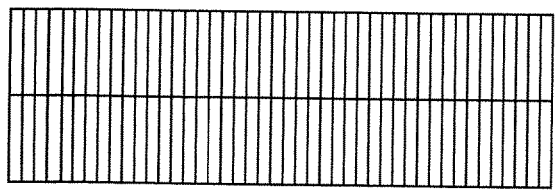
FIG. 10B illustrates the ground area allocated to plants in prior art row seeding.
Figure 10C:
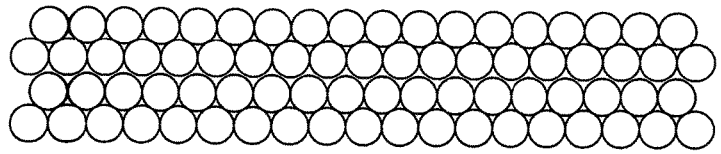
FIG. 10C illustrates a scheme for efficient placement of seeds.

FIG. 10B shows a schematic representation of the area allocated to each seed in prior art row seeders. The seeds are close together in the row direction and farther apart transverse to the row direction. This means that each plant is crowded in the row direction and needs to extend further to access solar insolation or soil resources in the transverse direction. FIG. 10O shows an alternative seeding scheme based on hexagonal close packing made possible by the present invention. The plants in the hexagonal packing scheme are able to use resources more efficiently.

Figure 10D:
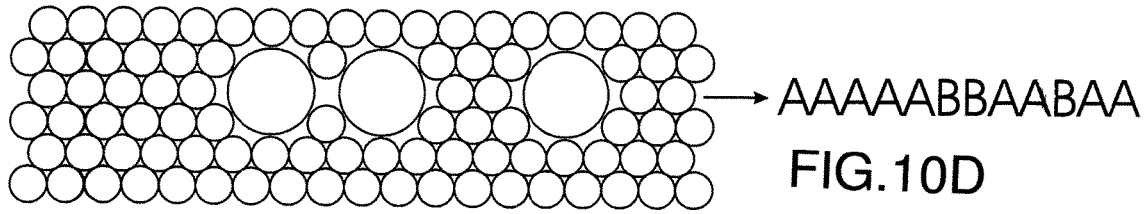
FIG. 10D illustrates a scheme for encoding position information in a pattern with two types of seeds.

FIG. 10D shows a schematic representation of a modified hexagonal close packed encoding method with two types of plants. The first type is read as an A and the second type is read as a B along the axis indicated. The unique sequence is compared with stored sequences to find the best match. Once a match is found, the identity of each seed in the sequence can be determined and the properties of each said seed retrieved for analysis as described above. Further, the identity of seeds that produced plants surrounding the unique sequence can be determined by counting the number of lattice intervals between a reference plant and an unknown plant along each lattice axis.

Figure 10E:
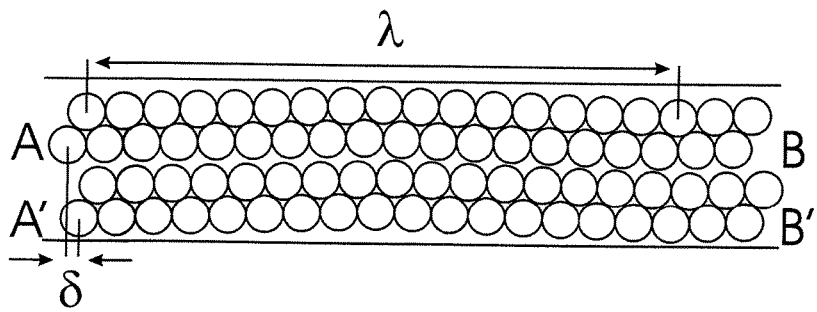
FIG. 10E illustrates a scheme for encoding position information in a pattern with one type of seeds using a transverse wave.

FIG. 10E shows an encoding method that can be used with a single type of plant based on a modified hexagonal close packed scheme. A triangle wave with wavelength $\lambda$ and two layers is shown running from A to B and a second wave with two layers is shown running from A' to B' offset by $\delta$. The phase difference $\delta/\lambda$ can be used to distinguish between layers transverse to the wave axis. The position of each seed is uniquely determined by its phase within the wave and relative to a reference point. Although the wavelengths of the two waves shown are equal in the diagram, the wavelengths need not be equal. One way to define a reference point is to arrange plant waves with different wavelengths to have common phase along a line transverse to the wave axis. Alternately, the reference point may be an external marker or beacon.

Figure 11:
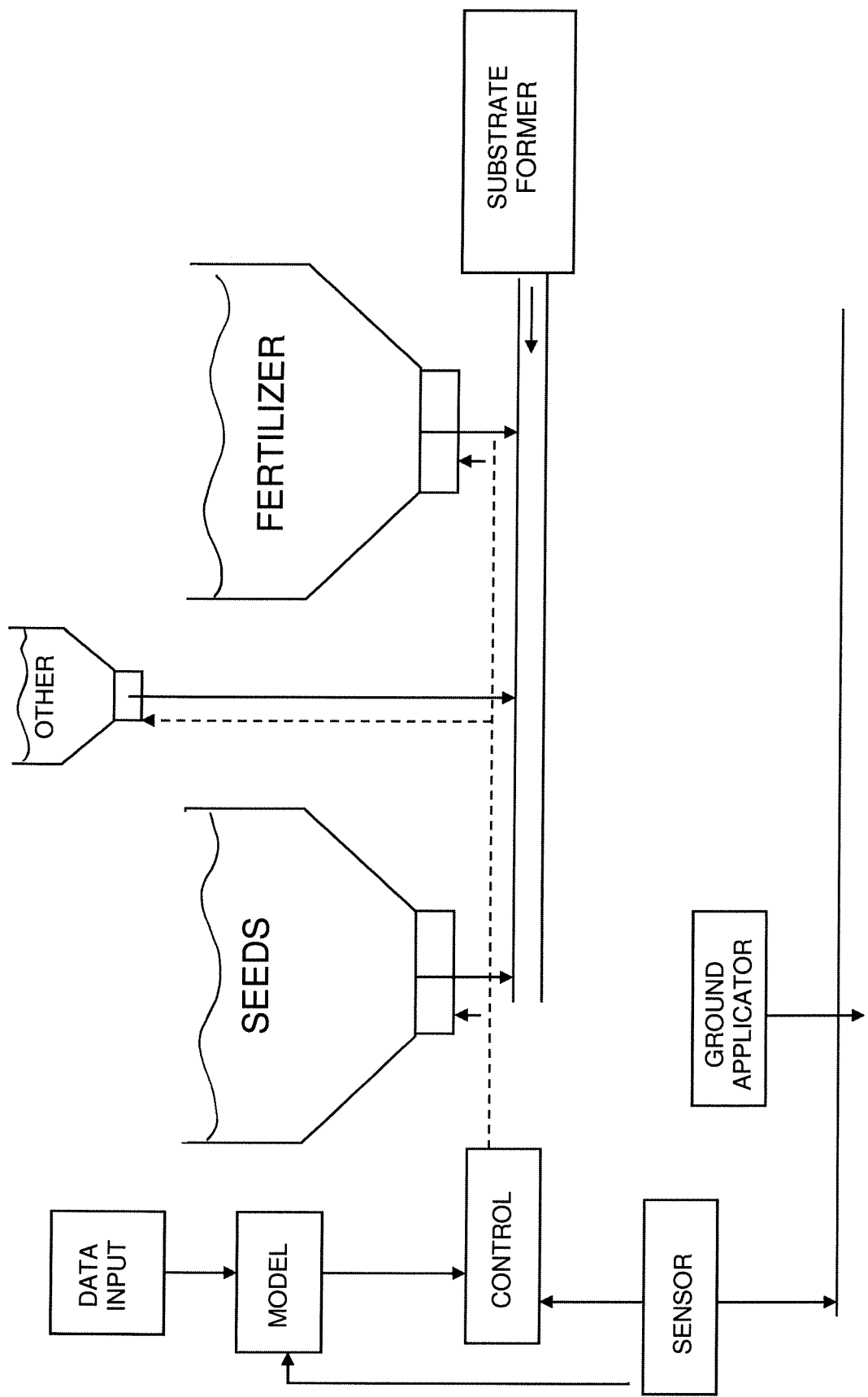
FIG. 11 is a schematic illustration of a seeding apparatus according to the present invention which creates and uses an intermediate substrate to apply controlled amounts and locations of seeds and other materials to the ground or other growth medium in a controlled pattern.

As shown in FIG. 11 an arrangement to deposit singulated particles from the singulation system on an intermediate substrate or carrier is provided. The intermediate substrate material functions to preserve spatial relationships between and among particles so deposited. A sensor measures one or more properties of the growth substrate or ground and the property information is used by a modeler module to predict crop properties for a plurality of trial particle arrangements and select a particle arrangement or prescription based on input data from the operator. The modeler invokes the agronomic modeler for each trial particle arrangement. The operator may, for example, specify that wheat, canola and peas are to be intercropped and request the modeler choose fertilizer inputs and seed locations for each type that maximizes the combined economic value if weather conditions are average. Alternately the operator may seek to minimize the effect of flooding or drought by selecting seed types and locations that produce minimal variance in total crop value over a wide range of weather conditions. The control unit generates signals to a substrate former and units to place seed, fertilizer and other inputs on the intermediate substrate according to the prescription from the modeler. The intermediate substrate material may be deposited on the ground or growth substrate at a later second time by a ground applicator in a manner that substantially transfers the spatial arrangement of particles on the intermediate substrate to the arrangement of the particles on the ground or growth substrate. For example, if seeds are transferred to an intermediate substrate at an interval of 10 mm, then the intermediate substrate is deposited on soil in a manner that the interval between seeds is also 10 mm. The intermediate substrate is subsequently placed on the ground by the ground applicator.

The substrate sensor of FIG. 11 may consist of one or more instruments that scan the substrate with spatial resolution on the scale of the root zone or canopy zone of a crop plant. The substrate sensor may measure the infrared spectrum and the raw spectrum is analyzed to provide information about the concentrations of water, nitrogen and phosphorous containing compounds in the soil or growth substrate. The substrate sensor may measure the dielectric response of the substrate to provide information about the moisture content. The substrate sensor may measure the Raman spectrum to provide information about minerals in the substrate. The substrate sensor may measure gamma rays from isotopes in the soil and analyze the intensity and energy to infer the concentrations of elements in the soil. The radio nucleide gamma emitters may be naturally occurring or generated, for example by neutron activation. The substrate sensor may measure laser induced breakdown spectra (LIBS) and the spectra are analyzed to provide information about the concentrations of elements in the substrate. The substrate sensor may transmit radio waves or acoustic waves and measure the reflections. The reflections are analyzed to provide information about the soil structure. The substrate sensor may be a camera and the images are analyzed to provide information about the number and size of stones or the quantity and type of crop residue. The information from the sensor or sensors is used by the agronomic model to predict the nutrition available to plants at the location. The modeler predicts plant growth with different choices of seed type and arrangement together with different choices of fertilizer and other agricultural agents at the location and selects the combination that best meets operator requirements.

FIGS. 12 to 15 show arrangements in which a longitudinally continuous substrate carrying seeds, fertilizer and other materials such as fungicide is applied to the ground as a strip. The intermediate substrate may be comprised, for example from materials such as polylactic acid, cellulose acetate, or similar materials. The term fertilizer used herein can of course relate to a crop growth enhancement material which can be used in this system. The materials applied as shown include the seed, fertilizer and a component which acts to control diffusion of the fertilizer toward the seeds. The fertilizer reservoirs can be located in different locations relative to the seed so as to temporally regulate the fertilizer available to the seed, in some cases using different materials at the different locations. For example, the distance between seed and fertilizer (or the diffusion constant of the material) can be varied according to expected or actual water availability. The intermediate carrier can include a barrier to diffusion to keep the material within the area of the seeds and to define a path for diffusion from a fertilizer reservoir and seed. The details of the seed and fertilizer arrangement may vary from location to location according to agronomic modeling for each location using sensor information from each location.

Figure 12:
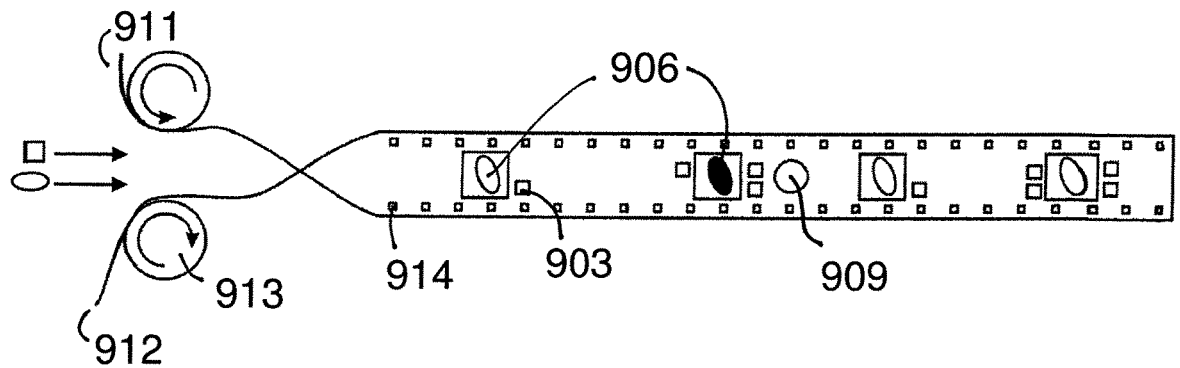
FIG. 12 shows an arrangement in which a longitudinally continuous substrate comprised of two layers carrying seeds, fertilizer and other materials such as a measurement device is applied to the ground as a strip.

In FIG. 12 the intermediate substrate is comprised of two layers 911 and 912 each fed over a roller 913 with sprockets to engage holes 914. The holes 914 serve as registration marks for guiding the intermediate substrate to a specified location on the growth substrate. Seeds 906, fertilizer 903 and other material 909 such as a measurement device are placed on first layer 911 at positions and quantifies determined by the agronomic algorithm based on at least one measured property for the location where the intermediate substrate is to be placed. The second layer 912 is placed over the first to hold the materials deposited in position.

Figure 13:
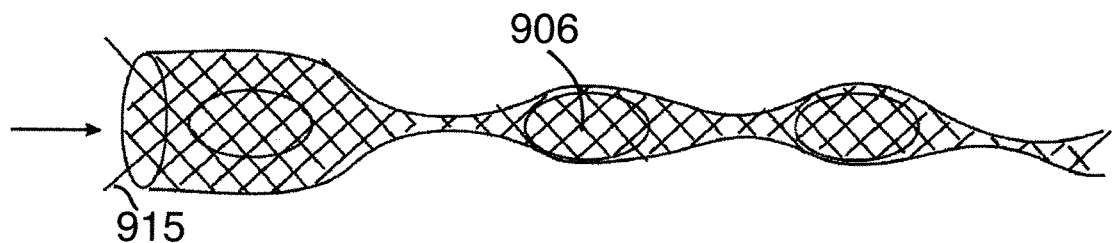
FIG. 13 shows an arrangement in which a longitudinally continuous substrate comprised of a braided tube carrying seeds, fertilizer and other materials is applied to the ground as a strip.

FIG. 13 shows an arrangement in which seeds 906 and other materials are confined at discrete positions by a variable diameter tube comprised of material 915 that is braided continuously to enclose the seeds. The material may be cellulose or nylon based for example. The intermediate substrate is selected so that it provides physical protection to the seeds.

Figure 14:
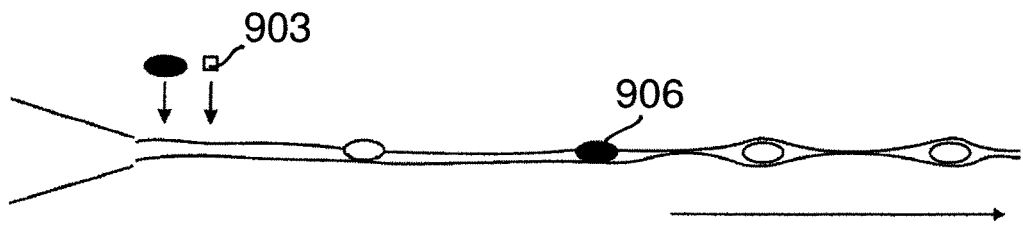
FIG. 14 shows an arrangement in which a longitudinally continuous substrate comprised of extruded material carrying seeds, fertilizer and other materials is applied to the ground as a strip.
Figure 15:
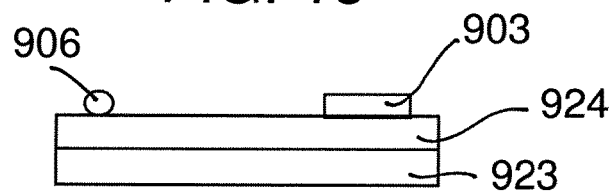
FIG. 15 shows an arrangement in which a longitudinally continuous substrate comprised of a tape with an adhesive layer carrying seeds, fertilizer and other materials such as fungicide is applied to the ground as a strip.
Figure 16:
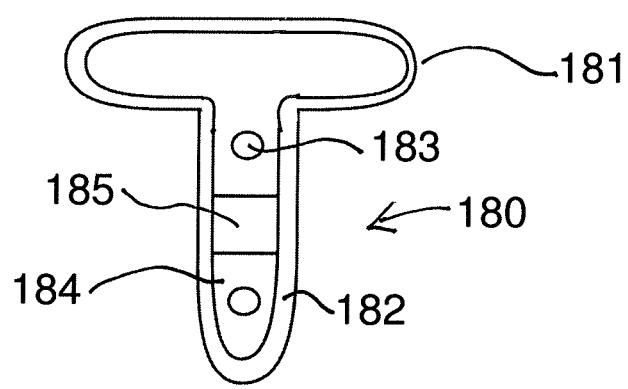
FIG. 16 shows an alternative construction of the intermediate substrate in the form of a series of separate plug members to be applied individually to the ground.
Figures 20A, 20B:
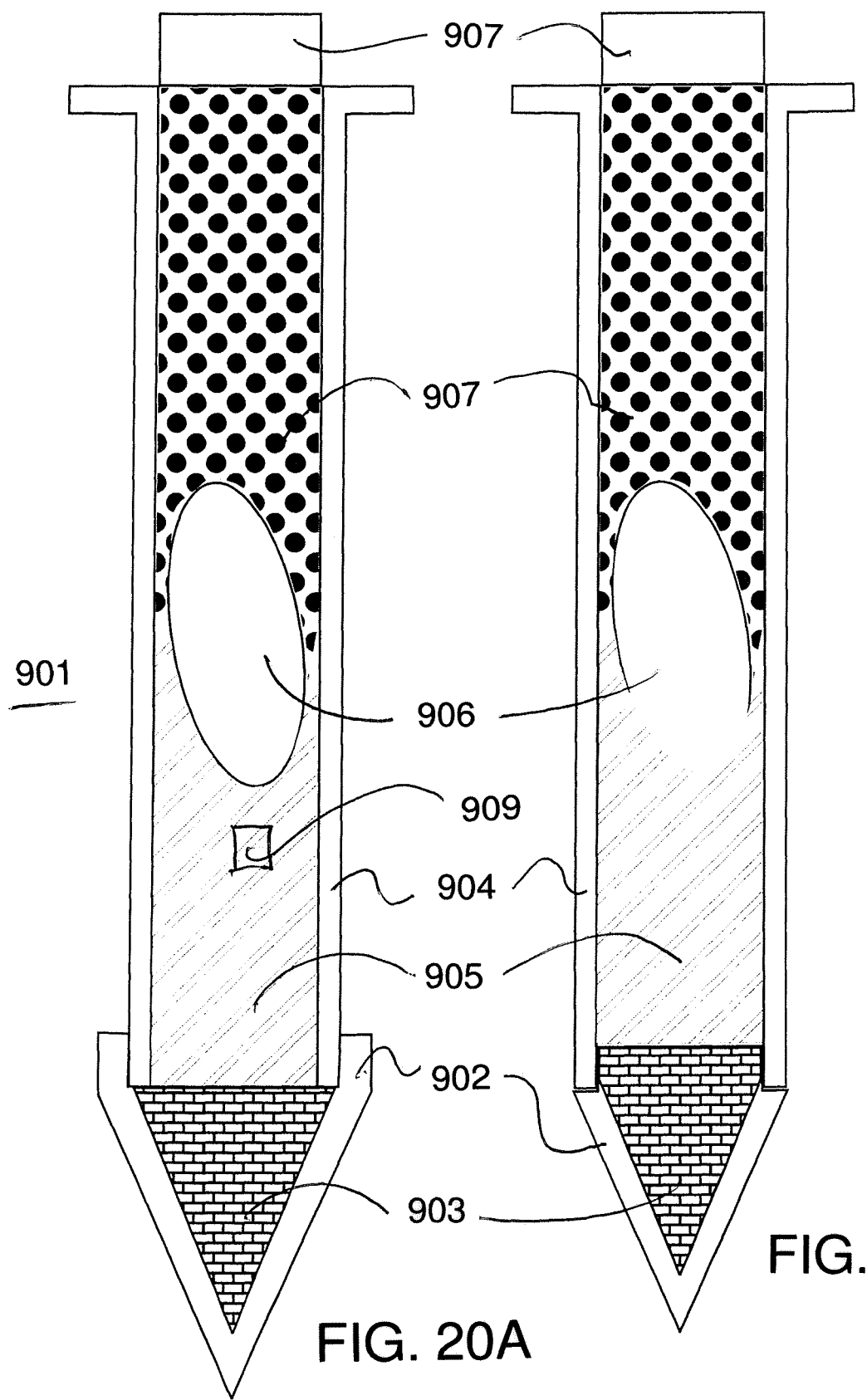
FIGS. 20A and 20B show in enlarged view two embodiments of the application plunger of FIGS. 18A to 18E.

FIG. 14 shows an arrangement in which the intermediate substrate is composed of a material 917 that increases viscosity following extrusion from nozzle 916. Seeds 906 and other materials are added while the substrate material is in a low viscosity state and become entrained in the flow. The seeds and other materials are held in place for deposition on the growth substrate as the intermediate substrate material increases viscosity and hardens. The intermediate substrate material can for example be a thermosetting polymer which may be of the type which is UV cured for rapid operation. Preferably the polymer is biodegradable. In some embodiments the fertilizer and other materials may be injected into the intermediate substrate material in solution form immediately prior to extrusion at concentrations specific to each seed and location.

FIG. 15 shows an arrangement wherein a tape material 923 with an adhesive coating 924 is dispensed and seeds 906 and fertilizer 903 or other materials are placed onto and held in place by the adhesive material. The tape material may be cellulose for example. Each seed or other material may be placed at arbitrary positions on the tape by for example translating the tape and moving a placement device transverse to the direction of motion and perpendicular to the tape plane.

FIG. 16 shows an alternative construction of the intermediate substrate in the form of a series of separate plug members to be applied individually to the ground. FIGS. 16 and 17 show seed plugs 180 with a shank 182 and a head 181. The shank contains seed 183 and fertilizer 184 separated by a diffusion control material 185. The plugs are fed to an applicator 186 in the form of a roller 187 with longitudinal slots each carrying a block 188 movable longitudinally in the slot. The block is loaded with a plug and the block is translated in the slot to a required position prior to ground engagement. As the roller rolls on the ground it pushes each plug into the ground at the location defined by its supporting block and the head is released leaving the plug in the ground. Computer control of the blocks in the slots both longitudinally of the roller and radially of the roller controls the location of placement of the plug in 2D. Placement in the longitudinal direction of movement is controlled by omitting some of the plugs from the available slots.

FIGS. 20A and 20B each show a seed plug 901 with detachable head 902 containing fertilizer 903 abutting the outer diameter of payload tube 904. Payload tube 904 contains a transport regulating medium 905 immediately adjacent to the fertilizer 903 that provides a plant germinating from seed 906 with a controlled rate of nutrition from fertilizer. The payload tube as shown includes a stop region 910 that limits the depth of penetration into the substrate. In an alternate arrangement, the payload tube may have an adjustable stop. In another alternative arrangement the payload tube may have no stop and be mounted on an XYZ stage for positioning the plug at any location and any depth.

The payload tube has loosely packed soil 907 positioned between the seed 906 and piston head 908. Piston head 908 retains the transport regulating medium, seed, and soil within payload tube 904 and may be used during tube loading to regulate soil packing so as to provide good contact between the seed and soil while not hindering sprout emergence. The requirements of each seed type will vary. The transport regulating medium 905 may contain hydroscopic substances that attract and retain soil moisture to aid the germination and development of the seed 906. The payload may include an optional diagnostic device 909 capable of making a measurement and communicating that measurement to an external reader. The diagnostic device could for example measure the concentration of nitrogen or phosphorous containing compounds in the root zone and relay the information via a radio link. The removable head may contain any combination of fertilizer, herbicide, fungicide, pesticide, a biological agent, or soil. The order of constituents within the payload tube is for illustrative purposes. The constituents may be placed within the payload tube and detachable head in any order. In FIG. 20A, the head 902 is located on the exterior of the tube 904 so that the head has portions contacting the exterior surface of the tube 904. In FIG. 20B the head is located at the end of the tube and held in place by the plug of fertilizer 903.

Figure 17:
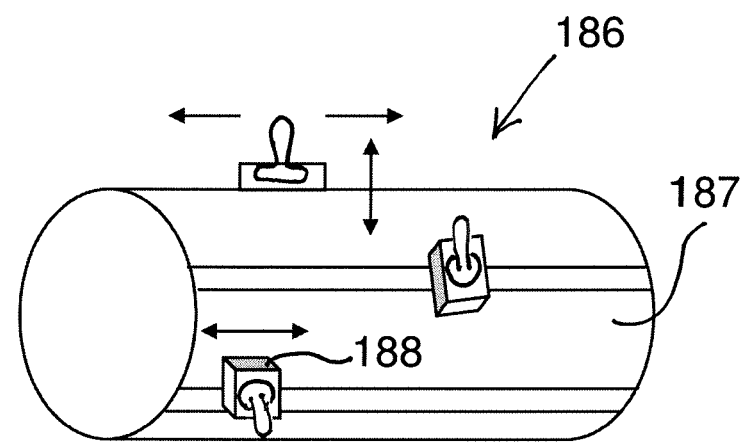
FIG. 17 shows an arrangement for applying the plugs of FIG. 18 to the ground at different positions in three orthogonal directions.
Figure 19:
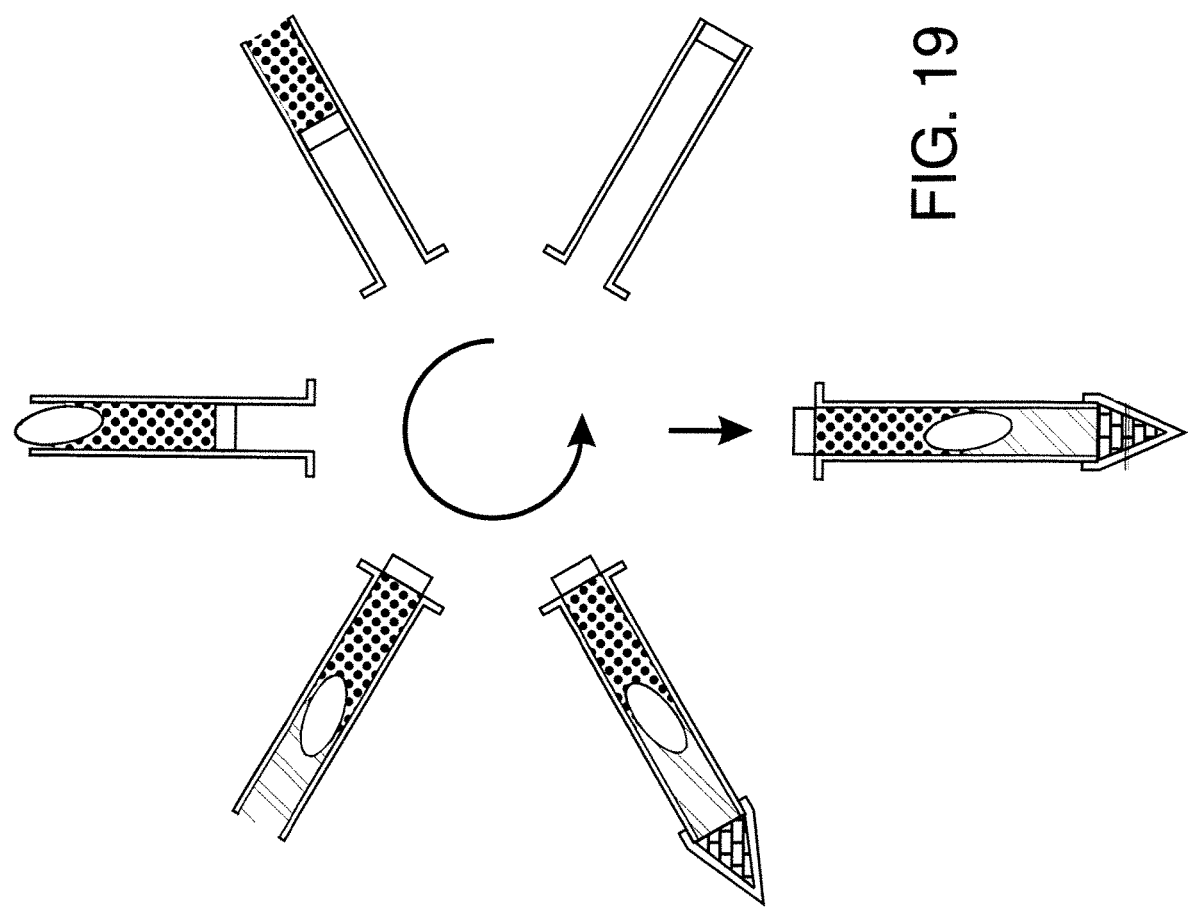
FIG. 19 shows separate stations of a filling station carried on the seeder where the application device is filled from supplies of the seeds and fertilizer carried on the seeder.

FIGS. 18A to 18E display a sequence for insertion of a plug as described in FIG. 20A into a growth substrate. The plug is positioned above the desired location in FIG. 18A and inserted vertically FIG. 18B until the tube stop is in contact with the substrate surface and the piston head is at the same level as the substrate surface as shown in FIG. 18C. In FIG. 18D the piston head remains at the level of the substrate surface and the payload tube is withdrawn from the substrate vertically leaving the detachable head and payload tube contents embedded in the substrate. Finally, the piston head is moved to the top of the payload tube (FIG. 18E) and the payload tube is reloaded as best shown in FIG. 19. The plug may be inserted as shown in FIG. 17. Alternately, the plug may be inserted from a XYZ platform mounted on the seeder. The seeder as a whole is translated in the X-direction. The plug is loaded on the XYZ platform and the platform translates in the Y direction to set the Y coordinate for plug placement. When the seeder reaches the desired X coordinate for plug placement, the platform is translated in the –X direction such that there is little or no relative motion between the ground and platform and the plug is inserted by platform translation in the Z direction. The XYZ platform may alternately move a seed tube and deposit a seed in the same manner.

The combine harvester component 700 of the system is shown in FIG. 21 and comprises tractor 701 forming a transport arrangement for movement across crops to be harvested mounted on ground wheels 702. The combine includes conventional components including a header 703 with cutter bar 704 and reel 705 supplying cut crop to feeder house 706. Inside the combine the fed crops are separated into grain and non-grain material by a beater 707, rotor 708 and sieve 709 so that the non-grain material is discharged from the rear at 710. The combine is operated by a worker in a cab 711 who has various control systems 712 to hand to control the various operations of the combine. A central processor 713 controls the operation of the system and receives signals from a location system 714.

The harvesting system on the combine thus includes components for collecting the crop and separating the grain from other crop material which is discharged.

The separated grain in this system is fed not directly to storage in a conventional combine but instead to a singulation, sensing and separating system 715 cooperating with the processor 713 and arranged to measure at least one property of each separate seed. The construction and operation of the singulation, sensing and separating system 715 is described in more detail hereinafter and is shown in the above PCT publication WO 2018/018155 which is incorporated by reference.

The sensing and separation system 715 acts to sort the seeds into separate paths 719 which in this embodiment lead to a number of separate bins 716, 717 and 718. In this embodiment the bins 716 and 717 are used as storage bins for transportation of the harvested material and the bin 718 is used to collect the best seeds for use in an attached seeding operation carried on the combine and shown at 720. The seeding system includes a tank 721 for the collected seeds, a singulator 722 which may be of the type disclosed herein and a ground planting system 723 for planting the singulated seeds. Fertilizer or other accessory materials can be added as indicated at 724. While the number of bins shown is relatively small, it will be appreciated that the system can include a whole array of bins each containing seeds having different characteristics so that the seeding system can select from any one of the array of bins depending on measured characteristics and measured requirements. The seeding system using the array can be either attached to and part of the harvester or can be a separate later seeding action but using the array of seeds from the bins generated by the above system. The seeds can be transferred from a storage bin on the harvester to a supply bin on the seeder or the array of bins can be transferred as a structure.

Regarding the quantity of containers, the system herein can act to sort large volumes of seeds into two or more containers, but in some scenarios the system will also be sorting smaller quantities into large array(s) of smaller containers. In one example of scale an array of containers could be 1000×1000 containers or more.

Also, each container can contain a minimum of one seed per container (for further analysis i.e. genetic) or each container could contain many seeds (i.e. all of the seeds from a particular plant or patch of similar plants that was harvesting for the purpose of seeding).

When planting seeds directly from the large array, the identity of the container that the seed came from would recorded as well as the location that the seed was planted and sample seeds (parent) would be saved in the container for further analysis (genetic) and comparison to the resulting children. That is, after the crop grows the system can go to the location of the specific plants in question and examine the results and compare the "parent" seed(s) with the "children". This technique can be extremely valuable for enhancing and accelerating plant breeding activities.

Also, the seeds in the array might not be harvested initially by the system. The seeds can be from seed companies wanting to plant thousands or millions of varieties efficiently on a single crop using our container array and plant position locating system as described above. Although the system would not be harvesting under this scenario, the system could still measure the properties of the seeds that are being planted and the system would keep track of the location (via planting pattern, GPS, RF tag on field or other position locating method).

Also shown in FIG. 21 is an auxiliary harvesting component 730 which is mounted in front of the header 703 so as to individually harvest selected plants from the field rather than feed them into the general harvest. This can be done by analyzing the plants in front of the header by a sensing system 731 such as a camera and imaging analysis system and by moving the auxillary harvesting component 730 across the header to the required location relative to the width of the header and to operate the system when the plants to be harvested are reached. This results in a selection of plants of a particular characteristic which are stored separately and may form the seeds for the planting system 720. The auxiliary harvesting component 730 includes a sorting mechanism of the type described above to select from the selected plants the best seeds for use in the seeding process or other purpose.

The arrangement shown in FIG. 21 and described herein can also be used in a method for harvesting crops where the substrate is used simultaneously for mixed crops of two or more different types planted and harvested simultaneously. Thus the machine 700 acts for harvesting the two or more crops previously planted and acts for separating required seeds of the two or more crops from other crop material using a common threshing system. Subsequent to the common harvesting the seeds of one of the crops are separated from the collected seeds of others of the collected crops. Preferably the collected elements are separated on a common machine with the harvesting using the separation system described in detail herein.

However as an alternative (not shown) the collected seeds are transported to a site separate from a harvesting machine and are separated at the separate site again using a stand-alone version of the system described herein.

The arrangement shown in FIG. 21 and described herein can also be used in a method for harvesting crops wherein two or more different crops are planted in the substrate and harvested using the machine 700 of FIG. 21. In this arrangement the seeding system used which is either the seeder 720 or a stand-alone seeding system of a conventional nature is operated during planting to place the different crops at set locations in a pattern or crop coding related to different locations in the substrate. Thus the pattern or code of type A and type B seeds can be laid out in a unique pattern related to the location at which the seeds are applied. During the harvesting the pattern or code in the crops is then detected and the location on the substrate determined by analyzing the pattern.

The system herein acts to separate not only A from B, but also different fractions of A and B so for example A+B→A1, A2, B1, B2

The harvester can identify the precise location of individual seeds from a prior seeding operation by a combination of one or more of GPS, position transponders, and the crop position encoding system described herein. This enables the system to associate the parameters of a seed placed at each location with the parameters of the crop plant and parts of the crop plant harvested. Thus the system allows a whole array of many thousands of different seed types to be individually seeded at identified locations. This can be done using a seeder with a large array of containers for different seed types where the seeder can take from any one of the containers and can place that selected seed at a required location with the resultant data recorded for use in later analysis. This can be done at harvesting or as a separate analysis step for example using drones. The arrangement herein also closes the circle in that it can operated to carry out the following steps:

(a) during seeding measure seed parameters
(b) during seeding measure location parameters
(c) during seeding place seed at measured location based on (a) and (b)
(d) during harvesting measure plant phenotype at location
(e) during harvesting harvest crop by location and separate seed from debris
(f) during harvesting measure seed parameters
(g) during harvesting direct seed to path based on (f)
(h) during harvesting store seed
(i) go to (a)

Note that the measurements at (a) and (f) can be different as a seed ages in storage losing vitality and germination potential due to the exhaustion of enzymes and energy reserves. By correlating the change from (f) to (a) with (d), we can statistically identify markers that predict germination potential for similar seeds.

Seeding operations use more seed than required for the target plant population to compensate for seeds that fail to germinate. By identifying vitality markers, seed requirements and cost can be reduced.

The pattern can be detected by measuring the harvested crops elements after harvesting using the sensing and separation system 715. As an alternative or in addition the pattern is detected by measuring the crops in advance of the harvesting using the sensing system 731.

The sensing and separation system 715 as described above and shown in FIGS. 2, 3 and 4 is mounted at a suitable location in the combine so as to receive the separated grain. This can for example be located at the typical elevator auger so that the material lifted from the sieves is carried upwardly but instead of entering the conventional single bin the material is fed to the feed tube 12 of the sensing and separation system.

The invention claimed is:

1. A method for growing crops in a growth medium comprising:
on a harvesting machine harvesting elements from crops in the growth medium;
using a common threshing system to separate the harvested elements from other crop material;
collecting the harvested elements from the common threshing system as a common supply of the separated harvested elements;
causing relative movement between the growth medium and the harvesting machine;
wherein there is provided a device for singulating the harvested elements from the common supply into a singulated stream of the harvested elements so that each harvested element is singulated from the other harvested elements into a singulated stream of the harvested elements for measurement,
using a sensing system to measure at least one property of each of the singulated elements independently of the other singulated elements while in the singulated stream;
dividing some of the singulated elements from others of the singulated elements into a separate path based on the property sensed;
and planting seeds from at least some of the collected elements in said growth medium.

2. The method according to claim 1 wherein the divided elements are directed to separate storage containers carried on the transport arrangement.

3. The method according to claim 1 wherein the sensing system comprises a device that receives a particule flux from each singulated element and performs the measurement which includes one or more of phontons, electrons, neutrons, atoms, ions, molecules, or any combination of the aforesaid.

4. The method according to claim 1 wherein the sensing system operates to obtain said at least one property from each singulated element which contains at least one quality parameter of each collected element which is analyzed to provide a classification of the collected elements.

5. The method according to claim 1 wherein a sensing system uses said least one property from each singulated element to identify the crop plant from which the harvested element is harvested.

6. The method according to claim 1 wherein the sensing system uses said least one property from each singulated element to identify a location from which the harvested element is harvested.

7. The method according to claim 1 wherein the sensing system uses said least one property from each singulated element to generate summary statistics of at least one measured property of the singulated elements in relation to one or more of a time the singulated element was harvested, a location the singulated element was harvested, a plant the singulated element was harvested from, a condition of the growth medium the singulated element was harvested from, or a stored property of a seed relating to the singulated element.

8. The method according to claim 1 wherein crops are planted on said growth medium at set locations in a pattern related to different locations in the growth medium and during harvesting detecting the pattern in the crops and determing a location on the growth medium by analyzing pattern.

9. The method according to claim 8 including dividing some of the singulated elements from others based on a location of the harvested plant.

10. The method according to claim 1 wherein said least one property from each singulated element in a sequence of singluated elements placed on the growth medium is stored along with information about the location the seeds were placed.

11. The method according to claim 1 including identifying a plant from a seed placed at a location on the growth medium and separating some of the singulated elements from others based on the identity of the plant.

12. The method according to claim 1 including an input by which end users communicate quality requirements and the singulated elements are divided into the separate paths using said least one property from each singulated element by changing classification criteria of said at least one property dedicated to the communicated quality requirements of the end user.

13. The method according to claim 1 including detecting phenotype parameters of the crops in advance of said harvesting.

14. A method according to claim 1 including detecting parameters of the growth medium with a sensor device mounted on the harvesting machine at a surface of the growth medium or sub-surface; and
    dividing some of the harvested elements from others of the harvested elements into a separate path based on the parameters sensed.

15. The method according to claim 1 wherein the singulated elements which are divided from others are weed seeds which are diverted to a weed seed bin.

16. The method according to claim 1 wherein there is provided an auxiliary harvesting unit to harvest separately elements on said growth medium taken from a selected plant or area based on one or more of seed, phenotype, location of the selected plant.

17. The method for growing crops in a growth medium comprising:
    on a harvesting machine harvesting machine harvesting elements from crops in the growth medium;
    causing relative movement between the growth medium and the harvesting machine;
    wherein there is provided a device for singulating the harvested elements into a singulated stream of the harvested elements so that each harvested element is singulated from the other harvested elements into a singulated stream of the harvested elements for measurement,
    using a sensing system to measure at least one property of each the singulated elements indepently of the other harvested elements while in the singulated stream;
    dividing some of the singulated elements from others of the singulated elements into a separate path based on the property sensed;
    and planting seeds from at least some of the collected elements in said growth medium;
    wherein the sensing system comprises a device that receives a particle flux from each singulated element and performs the measurement which includes one or more of photons, electrons, neutrons, atoms, ions, molecules, or any combination of the aforesaid.

18. The method for growing crops in a growth medium comprising:
    on a harvesting machine harvesting elements from crops in the growth medium;
    causing relative movement between the growth medium and the harvesting machine;
    wherein there is provided a device for singulating the harvested elements into a singulated stream of the harvested elements so that each harvested element is singulated from the other harvested elements into a singulated stream of the harvested elements for measurement,
    using a sensing system to measure at least one property of each the singulated elements independently of the other harvested elements while in the singulated stream;
    dividing some of the singulated elements from others of the singulated elements into a separate path based on the property sensed;
    and planting seeds from at least some of the collected elements in said growth medium;
    and identifying a plant from a seed placed at a location on the growth medium and separating some of the singulated elements from others based on the identity of the plant.

19. A method for growing crops in a growth medium comprising:
    on a harvesting machine harvesting elements from crops in the growth medium;
    causing relative movement between the growth medium and the harvesting machine;
    wherein there is provided a device for singulating the harvested elements into a singulated stream of the harvested elements so that each harvested element is singulated from the other harvested elements into a singulated stream of the harvested elements for measurement,
    using a sensing system to measure at least one property of each the signulated elements independently of the other harvested elements while in the singulated stream;
    dividing some of the singulated elements from others of the singulated elements into a separate path based on the property sensed;

and planting seeds from at least some of the collected elements in said growth medium;

wherein there is provided an input by which end users communicate qauality requirements and the singulated elements are divided into the separate paths using said least one property from each singulated element by changing classification criteria of said at least one property dedicated to the communicate quality requirements of the end user.

* * * * *